United States Patent
Blackaby et al.

(10) Patent No.: US 6,642,229 B2
(45) Date of Patent: Nov. 4, 2003

(54) 3-PHENYL-IMIDAZO-PYRIMIDINE DERIVATIVES AS LIGANDS FOR GABA RECEPTORS

(75) Inventors: Wesley Peter Blackaby, Buckhurst Hill (GB); Simon Charles Goodacre, Benington (GB); David James Hallett, Watford (GB); Andrew Jennings, Sawbridgworth (GB); Richard Thomas Lewis, Bishop's Stortford (GB); Kevin William Moore, Buntingford (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/296,116

(22) PCT Filed: May 17, 2001

(86) PCT No.: PCT/GB01/02158

§ 371 (c)(1),
(2), (4) Date: Nov. 22, 2002

(87) PCT Pub. No.: WO01/90108

PCT Pub. Date: Nov. 29, 2001

(65) Prior Publication Data

US 2003/0176449 A1 Sep. 18, 2003

(51) Int. Cl.[7] ..................... A61K 31/5337; A61P 25/22; C07D 487/04
(52) U.S. Cl. ..................... 514/233.2; 544/117; 544/238; 544/263
(58) Field of Search ................. 544/117, 238, 544/263; 514/733.2

(56) References Cited

FOREIGN PATENT DOCUMENTS

| EP | 0 563 001 | 3/1993 |
|---|---|---|
| EP | 0 616 807 | 3/1994 |
| WO | WO 96/33191 | 10/1996 |
| WO | WO 99/19323 | 4/1999 |
| WO | WO 99/36423 | 7/1999 |

OTHER PUBLICATIONS

Sieghart, W: Pharmacological Reviews, Williams and Wilkins Inc., Baltimore, MD, US, vol. 47, No. 2, 1995, pp. 181–234, ISSN; 0031–6997.

Teuber, L et al: Current Pharmaceutical Design, Bentham Science Publishers, vol. 5, 1999, pp. 317–343 ISSN: 1381–6128.

Tully, R. et al: Drug Development Res., vol. 22, 1991, pp. 299–308, New York.

Zhang, P et al: Medicinal Chemistry Research, Birkhaeuser, Boston, US, vol. 5, No. 7, 1995, pp. 487–495, ISSN; 1054–2523.

Martin et al., Expert Opinion On Therapeutic Patents, Ashley Publications, GB, vol. 9, No. 10, 1999, pp. 1347–1358.

Primary Examiner—Robert W. Ramsuer
(74) Attorney, Agent, or Firm—J. Eric Thies; Melvin Winokur

(57) ABSTRACT

A class of 3-phenylimidazo(1,2-a)pyrimidine derivatives (of Formula I, or salt or prodrug thereof: I) wherein Y represents a chemical bond, an oxygen atom, or a —NH— linkage; Z represents an optionally substituted aryl or heteroaryl group; $R^1$ represents hydrogen, hydrocarbon, a heterocyclic group, halogen, cyano trifluoromethyl, nitro, —$OR^a$, —$SR^a$, —$SOR^a$, —$SO_2R^a$, —$SO^2NR^aR^b$, —$NR^aR^b$, —$NR^aCOR^b$, —$NR^aCO_2R^b$, —$COR^a$, $CO_2R^a$, —$CONR^aR^b$ or —$CR^a$=$NOR^b$; and $R^a$ and $R^b$ independently represent hydrogen, hydrocarbon or a heterocyclic group.), substituted at the meta position of the phenyl ring by an optionally substituted aryl or heteroaryl group which is directly attached or bridged by an oxygen atom or a —NH— linkage, are selective ligands for $GABA_A$ receptors, in particular having good affinity for the a2 and/or a3 and/or a5 subunit thereof, and are accordingly of benefit in the treatment and/or prevention of adverse conditions of the central nervous system, including anxiety, convulsions and cognitive disorders.

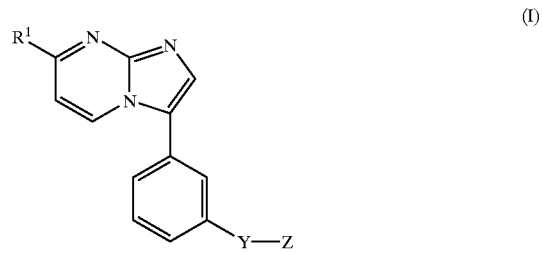

(I)

11 Claims, No Drawings

3-PHENYL-IMIDAZO-PYRIMIDINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB01/02158, filed May 17, 2001, which claims priority under 35 U.S.C. §119 from GB Application No. 0012709.2, filed May 24, 2000 and GB Application No. 0107137.2, filed Mar. 24, 2001.

The present invention relates to a class of substituted imidazopyrimidine derivatives and to their use in therapy. More particularly, this invention is concerned with imidazo[1,2-a]pyrimidine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta\gamma 1$, $\alpha 2\beta 2/3\gamma 2$, $\alpha 3\beta\gamma 2/3$, $\alpha 4\beta\delta$, $\alpha 5\beta 3\gamma 2/3$, $\alpha 6\beta\gamma 2$ and $\alpha 6\beta\delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Moreover, agents which are inverse agonists of the $\alpha 5$ subunit are likely to be beneficial in enhancing cognition, for example in subjects suffering from dementing conditions such as Alzheimer's disease. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; and hearing disorders, including tinnitus and age-related hearing impairment.

Selective ligands for $GABA_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human $GABA_A$ receptor.

The present invention provides a class of imidazopyrimidine derivatives which possess desirable binding properties at various $GABA_A$ receptor subtypes. The compounds in accordance with the present invention have good affinity as ligands for the α2 and/or α3 and/or α5 subunit of the human $GABA_A$ receptor. The compounds of this invention may interact more favourably with the α2 and/or α3 subunit than with the α1 subunit; and/or may interact more favourably with the α5 subunit than with the α1 subunit.

The compounds of the present invention are $GABA_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

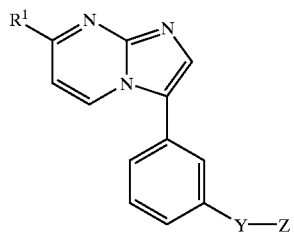

(I)

wherein

Y represents a chemical bond, an oxygen atom, or a —NH— linkage;

Z represents an optionally substituted aryl or heteroaryl group;

$R^1$ represents hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents.

Suitably, the group Z is unsubstituted or monosubstituted. Illustrative substituents on the group Z include halogen, cyano, trifluoromethyl, nitro, $C_{1-6}$ alkoxy, amino, formyl, $C_{2-6}$ alkoxycarbonyl, methyloxadiazolyl, triazolyl and —$CR^a$=$NOR^b$, wherein $R^a$ and $R^b$ are as defined above. Typical substituents on the group Z include halogen, cyano, nitro, amino, formyl, $C_{2-6}$ alkoxycarbonyl and —$CR^a$=$NOR^b$.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

A typical C3-7 heterocycloalkyl($C_{1-6}$)alkyl group is morpholinylmethyl.

Suitable heteroaryl groups include pyridinyl, quinolinyl, isoquinolinyl, pyridazinyl, pyrimidinyl, pyrazinyl, furyl, benzofuryl, dibenzofrryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^VR^W$, $-NR^VCOR^W$, $-NR^VCO_2R^W$, $-NR^VSO_2R^W$, $-CH_2NR^VSO_2R^W$, $-NHCONR^VR^W$, $-CONR^VR^W$, $-SO_2NR^VR^W$ and $-CH_2SO_2NR^VR^W$, in which $R^V$ and $R^W$ independently represent hydrogen, $C_{1-6}$ alkyl, aryl or aryl ($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In a preferred embodiment, Y represents a chemical bond.

In another embodiment, Y represents an oxygen atom.

In a further embodiment, Y represents a —NH— linkage.

Representative values for the substituent Z include phenyl, pyridinyl, thienyl, thiazolyl, imidazolyl and triazolyl, any of which groups may be optionally substituted. Typical values of Z include phenyl, pyridinyl, thienyl and thiazolyl, any of which groups may be optionally substituted. In a favoured embodiment, Z represents an optionally substituted phenyl group, in particular monosubstituted phenyl. In another embodiment, Z represents optionally substituted pyridinyl, especially pyridin-2-yl or pyridin-3-yl.

Examples of suitable substituents on the group Z include fluoro, chloro, cyano, trifluoromethyl, nitro, methoxy, amino, formyl, methoxycarbonyl, methyloxadiazolyl, triazolyl and —CH=NOH. Examples of typical substituents on the group Z include chloro, cyano, nitro, amino, formyl, methoxycarbonyl and —CH=NOH. Examples of particular substituents on the group Z include fluoro, cyano, trifluoromethyl, methoxy, methyloxadiazolyl, triazolyl and —CH=NOH; especially fluoro or cyano; and more especially cyano.

Illustrative values of Z include fluorophenyl, cyanophenyl, (cyano)(fluoro)phenyl, trifluoromethyl-phenyl, nitrophenyl, methoxyphenyl, methyloxadiazolyl-phenyl, triazolyl-phenyl, phenyl-CH=NOH, pyridinyl, (amino)(chloro)pyridiinyl, cyano-pyridinyl, cyano-thienyl, formyl-thienyl, methoxycarbonyl-thienyl, thienyl-CH=NOH, thiazolyl, imidazolyl and triazolyl. Specific values of Z include cyanophenyl, nitrophenyl, pyridinyl, (amino)(chloro)pyridinyl, cyano-thienyl, formyl-thienyl, methoxycarbonyl-thienyl, thienyl-CH=NOH and thiazolyl. Individual values of Z include fluorophenyl, cyanophenyl, (cyano)(fluoro)phenyl, trifluoromethyl-phenyl, methoxyphenyl, methyloxadiazolyl-phenyl, triazolyl-phenyl, phenyl-CH=NOH, pyridinyl, cyano-pyridinyl, thiazolyl, imidazolyl and triazolyl.

A particular value of Z is cyanophenyl, especially 2-cyanophenyl.

Typically, $R^1$ represents hydrogen, hydrocarbon, a heterocyclic group, halogen, cyano, trifluoromethyl, $-OR^a$, $-COR^a$, $-CO_2R^a$ or $-CR^a=NOR^b$. Suitably, $R^1$ represents hydrocarbon, a heterocyclic group, halogen, triiluoromethyl, $-OR^a$, $-COR^a$, $-CO_2R^a$ or $-CR^a=NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Representative values of $R^1$ include hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, $C_{3-7}$ heterocycloalkyl($C_{1-6}$)alkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl and $-CR^a=NOR^b$, in which $R^a$ and $R^b$ are as defined above. Typical values of $R^1$ include hydrogen, $C_{1-6}$ alkyl, halo($C_{1-6}$)alkyl, dihalo($C_{1-6}$)alkyl, hydroxy($C_{1-6}$)alkyl, di($C_{1-6}$)alkoxy($C_{1-6}$)alkyl, $C_{3-7}$ cycloalkyl, $C_{37}$ heterocycloalkyl($C_{1-6}$)alkyl, heteroaryl($C_{1-6}$)alkyl, cyano, trifluoromethyl, $C_{1-6}$ alkoxy, formyl, $C_{2-6}$ alkylcarbonyl, $C_{2-6}$ alkoxycarbonyl and $-CR^a=NOR^b$, in which $R^a$ and $R^b$ are as defined above. Illustrative values of $R^1$ include $C_{1-6}$ alkyl, hydroxy($C_{1-6}$)alkyl, heteroaryl, halogen, triiluoromethyl, $C_{1-6}$ alkoxy, formyl, $C_{2-6}$ alkylcarbonyl, $C_{2-6}$ alkoxycarbonyl and $-CR^a=NOR^b$, in which $R^a$ and $R^b$ are as defined above.

Itemised values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, cyclopropyl, cyclobutyl, morpholinylmethyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl.

Selected values of $R^1$ include hydrogen, methyl, fluoromethyl, difluoromethyl, hydroxymethyl, dimethoxymethyl, dimethoxyethyl (especially 1,1-dimethoxyethyl), isopropyl, hydroxypropyl (especially 2-hydroxyprop-2-yl), tert-butyl, cyclopropyl, cyclobutyl, morpholinylmethyl, triazolylmethyl, cyano, trifluoromethyl, methoxy, formyl, acetyl, methoxycarbonyl and —$CR^2$=$NOR^3$, in which $R^2$ and $R^3$ are as defined above.

Individual values of $R^1$ include hydrogen, methyl, fluoromethyl, difluoromethyl, hydroxymethyl, dimethoxymethyl, dimethoxyethyl (especially 1,1-dimethoxyethyl), isopropyl, tert-butyl, cyclopropyl, cyclobutyl, morpholinylmethyl, triazolylmethyl, cyano, trifluoromethyl, methoxy, formyl, acetyl, methoxycarbonyl and —$CR^2$=$NOR^3$, in which $R^2$ and $R^3$ are as defined above.

Specific values of $R^1$ include methyl, hydroxymethyl, hydroxyethyl, furyl, chloro, trifluoromethyl, methoxy, formyl, acetyl, methoxycarbonyl and —$CR^2$=$NOR^3$, in which $R^2$ and $R^3$ are as defined above.

A particular value of $R^1$ is $C_{1-6}$ alkyl, especially methyl.

In one favoured embodiment, $R^1$ represents 2-hydroxyprop-2-yl. In another favoured embodiment, $R^1$ represents trifluoromethyl.

Suitably, $R^2$ is hydrogen.

Suitably, $R^3$ represents hydrogen or dimethylaminoethyl, especially hydrogen.

A particular sub-class of compounds according to the invention is represented by the compounds of formula IIA, and salts and prodrugs thereof:

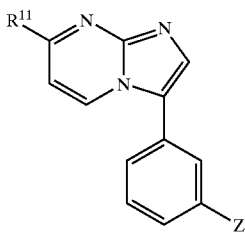

(IIA)

wherein
Z is as defined above;
$R^{11}$ represents hydrogen, $C_{1-6}$ alkyl, halo($C_{1-6}$)allyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, $C_{3-7}$ heterocycloalkyl($C_{1-6}$)alkyl, heteroaryl, $C_{1-6}$ alkylheteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl or —$CR^4$=$NOR^5$;
$R^4$ represents hydrogen or $C_{1-6}$ alkyl; and
$R^5$ represents hydrogen, $C_{1-6}$ alkyl, hydroxy($C_{1-6}$)alkyl or di($C_{1-6}$)alkylamino(($C_{1-6}$)alkyl.

The present invention also provides a compound of formula IIA as depicted above, or a salt or prodrug thereof, wherein $R^{11}$ represents $C_{1-6}$ alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl or —$CR^4$=$NOR^5$; and Z, $R^4$ and $R^5$ are as defined above.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents $C_{3-7}$ heterocycloalkyl($C_{1-6}$)alkyl, this group is suitably morpholinylmethyl.

Where $R^{11}$ represents heteroaryl, this group is suitably pyridinyl, furyl, thienyl or oxazolyl, especially furyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Typical values of $R^{11}$ include hydrogen, $C_{1-6}$ alkyl, halo($C_{1-6}$)alkyl, dihalo($C_{1-6}$)alkyl, hydroxy($C_{1-6}$)alkyl, di($C_{1-6}$) alkoxy($C_{1-6}$)alkyl, $C_{3-7}$ cycloalkyl, $C_{3-7}$ heterocycloalkyl ($C_{1-6}$)alkyl, heteroaryl($C_{1-6}$)alkyl, cyano, trifluoromethyl, $C_{1-6}$ alkoxy, formyl, $C_{2-6}$ alkylcarbonyl, $C_{2-6}$ alkoxycarbonyl and —$CR^4$=$NOR^5$, in which $R^4$ and $R^5$ are as defined above.

Itemised values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, cyclopropyl, cyclobutyl, morpholinylmethyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ and $R^3$ are as defined above.

Selected values of $R^{11}$ include hydrogen, methyl, fluoromethyl, difluoromethyl, hydroxymethyl, dimethoxymethyl, dimethoxyethyl (especially 1,1-dimethoxyethyl), isopropyl, hydroxypropyl (especially 2-hydroxyprop-2-yl), tert-butyl, cyclopropyl, cyclobutyl, morpholinylmethyl, triazolylmethyl, cyano, trifluoromethyl, methoxy, formyl, acetyl, methoxycarbonyl and —$CR^2$=$NOR^3$, in which $R^2$ and $R^3$ are as defined above.

Individual values of $R^{11}$ include hydrogen, methyl, fluoromethyl, difluoromethyl, hydroxymethyl, dimethoxymethyl, dimethoxyethyl (especially 1,1-dimethoxyethyl), isopropyl, tert-butyl, cyclopropyl, cyclobutyl, morpholinylmethyl, triazolylmethyl, cyano, trifluoromethyl, methoxy, formyl, acetyl, methoxycarbonyl and —$CR^2$=$NOR^3$, in which $R^2$ and $R^3$ are as defined above.

Representative values of $R^{11}$ include methyl, hydroxymethyl, hydroxyethyl, furyl, chloro, trifluoromethyl, methoxy, formyl, acetyl, methoxycarbonyl and —$CR^2$=$NOR^3$, in which $R^2$ and $R^3$ are as defined above.

A particular value of $R^{11}$ is $C_{1-6}$ alkyl, especially methyl.

In one favoured embodiment, $R^{11}$ represents 2-hydroxyprop-2-yl. In another favoured embodiment, $R^{11}$ represents trifluoromethyl.

One representative subset of the compounds of formula IIA above is represented by the compounds of formula IIB, and salts and prodrugs thereof:

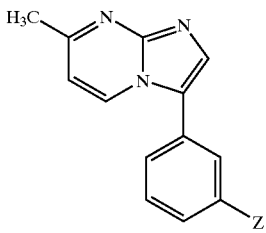

(IIB)

wherein Z is as defined above.

Another representative subset of the compounds of formula IIA above is represented by the compounds of formula IIC, and salts and prodrugs thereof:

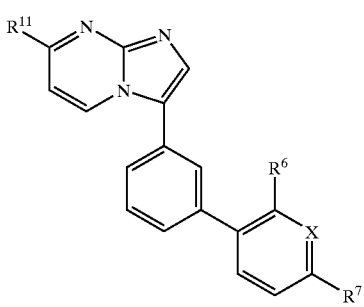

(IIC)

wherein
X represents CH or N;
$R^6$ represents fluoro, cyano, trifluoromethyl, methoxy, methyloxadiazolyl, triazolyl or —$CR^2$=$NOR^3$;
$R^7$ represents hydrogen or fluoro; and
$R^2$, $R^3$ and $R^{11}$ are as defined above.

In a favoured embodiment, X represents CH. In another embodiment, X represents N.

In a particular embodiment, $R^6$ represents cyano.

In one embodiment, $R^7$ is hydrogen. In another embodiment, $R^7$ is fluoro.

In a specific embodiment of the compounds of formula IIC, X is CH, $R^6$ is cyano, and $R^7$ is hydrogen.

A further representative subset of the compounds of formula IIA above is represented by the compounds of formula IID, and salts and prodrugs thereof:

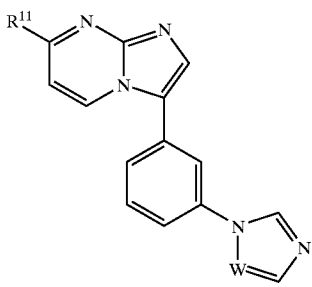

(IID)

wherein
W represents CH or N; and
$R^{11}$ is as defined above.

In one embodiment, W represents CH. In another embodiment, W represents N.

In relation to formula IID above, the substituent $R^{11}$ favourably represents trifluoromethyl.

Specific compounds within the scope of the present invention include:
3'-(7-methylimidazo[1,2-a]pyrimidin-3-yl)biphenyl-2-carbonitrile;
3'-(imidazo[1,2-a]pyrimidin-3-yl)biphenyl-2-carbonitrile;
3'-(7-trifluoromethylimidazo[1,2-a]pyrimidin-3-yl)biphenyl-2-carbonitrile;
3'-[7-(1,1-dimethoxyethyl)imidazo[1,2-a]pyrimidin-3-yl]biphenyl-2-carbonitrile;
3'-(7-acetylimidazo[1,2-a]pyrimidin-3-yl)biphenyl-2-carbonitrile;
3'-(7-isopropylimidazo[1,2-a]pyrimidin-3-yl)biphenyl-2-carbonitrile;
3'-(7-cyclopropylimidazo[1,2-a]pyrimidin-3-yl)biphenyl-2-carbonitrile;
3'-(7-tert-butylimidazo[1,2-a]pyrimidin-3-yl)biphenyl-2-carbonitrile;
3'-(7-cyclobutylimidazo[1,2-a]pyrimidin-3-yl)biphenyl-2-carbonitrile;
3'-(7-methoxyimidazo[1,2-a]pyrimidin-3-yl)biphenyl-2-carbonitrile;
3'-(7-hydroxymethylimidazo[1,2-a]pyrimidin-3-yl)biphenyl-2-carbonitrile;
3'-(7-fluoromethylimidazo[1,2-a]pyrimidin-3-yl)biphenyl-2-carbonitrile;
3'-(7-formylimidazo[1,2-a]pyrimidin-3-yl)biphenyl-2-carbonitrile;
3'-(7-hydroxyiminomethylimidazo[1,2-a]pyrimidin-3-yl)biphenyl-2-carbonitrile;
3-(2'-cyanobiphenyl-3-yl)imidazo[1,2-a]pyrimidine-7-carbonitrile;
3-(2'-methoxybiphenyl-3-yl)-7-methylimidazo[1,2-a]pyrimidine;
3-(2'-cyanobiphenyl-3-yl)imidazo[1,2-a]pyrimidine-7-carboxylic acid methyl ester;
3'-(7-dimethoxymethylimidazo[1,2-a]pyrimidin-3-yl)biphenyl-2-carbonitrile;
3'-[7-([1,2,4]triazol-1-ylmethyl)imidazo[1,2-a]pyrimidin-3-yl]biphenyl-2-carbonitrile;
3'-(7-difluoromethylimidazo[1,2-a]pyrimidin-3-yl)biphenyl-2-carbonitrile;
7-methyl-3-[3-(pyridin-3-yl)phenyl]imidazo[1,2-a]pyrimidine;
7-methyl-3-[3'-(5-methyl-[1,2,4]oxadiazol-3-yl)biphenyl-3-yl]imidazo[1,2-a]pyrimidine;
7-methyl-3-[2'-(3-methyl-[1,2,4]oxadiazol-5-yl)biphenyl-3-yl]imidazo[1,2-a]pyrimidine;
7-methyl-3-[3-(thiazol-4-yl)phenyl]imidazo[1,2-a]pyrimidine;
3'-(7-methylimidazo[1,2-a]pyrimidin-3-yl)biphenyl-2-carbaldehyde oxime;
3-[3-(7-methylimidazo[1,2-a]pyrimidin-3-yl)phenyl]pyridine-2-carbonitrile;
7-methyl-3-[3-(pyridin-2-yl)phenyl]imidazo[1,2-a]pyrimidine;
7-methyl-3-[3-(thiazol-2-yl)phenyl]imidazo[1,2-a]pyrimidine;
7-methyl-3-(2'-trifluoromethylbiphenyl-3-yl)imidazo[1,2-a]pyrimidine;
3-(2'-fluorobiphenyl-3-yl)-7-methylimidazo[1,2-a]pyrimidine;

4-fluoro-3'-(7-methylimidazo[1,2-a]pyrimidin-3-yl)biphenyl-2-carbonitrile;
3-[3-(imidazol-1-yl)phenyl]-7-trifluoromethylimidazo[1,2-a]pyrimidine;
3-[3-([1,2,4]triazol-1-yl)phenyl]-7-trifluoromethylimidazo[1,2-a]pyrimidine;
3-[2'-([1,2,4]triazol-1-yl)biphenyl-3-yl]-7-trifluoromethylimidazo[1,2-a]pyrimidine;
3'-[7-(morpholin-4-ylmethyl)imidazo[1,2-a]pyrimidin-3-yl]biphenyl-2-carbonitrile;
4-fluoro-3'-(7-trifluoromethylimidazo[1,2-a]pyrimidin-3-yl)biphenyl-2-carbonitrile;
4-fluoro-3'-[7-(2-hydroxyprop-2-yl)imidazo[1,2-a]pyrimidin-3-yl]biphenyl-2-carbonitrile;
3-[3-(pyridin-3-yl)phenyl]-7-trifluoromethylimidazo[1,2-a]pyrimidine;
3-[3-([1,2,4]triazol-4-yl)phenyl]-7-trifluoromethylimidazo[1,2-a]pyrimidine;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the $\alpha 3$ subunit of the human $GABA_A$ receptor is conveniently as measured in the assay described hereinbelow. The $\alpha 3$ subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the $\alpha 3$ subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the $\alpha 1$ subunit of the human $GABA_A$ receptor.

The potentiation of the GABA $EC_{20}$ response in stably transfected cell lines expressing the $\alpha 3$ and $\alpha 1$ subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

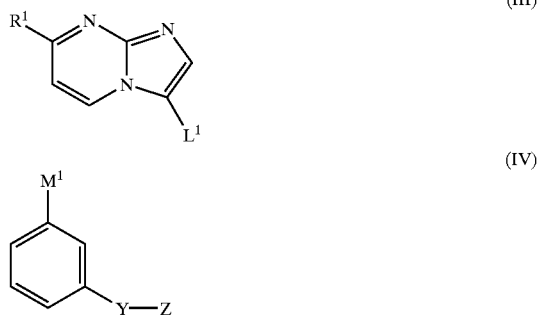

wherein Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis(triphenylphosphine)-palladium(0). The reaction is conveniently carried out at an elevated temperature in a solvent such as N,N-dimethylacetamide, 1,4-dioxane or tetrahydrofuran, advantageously in the presence of potassium phosphate, copper(I) iodide or sodium carbonate. Alternatively, the transition metal catalyst employed may be dichloro[1,1'-bis(diphenylphosphino)-ferrocene]palladium (II), in which case the reaction is conveniently effected at an elevated temperature in a solvent such as N,N-dimethylformamide.

In an alternative procedure, the compounds according to the present invention may be prepared by a process which comprises reacting a compound of formula V with a compound of formula VI:

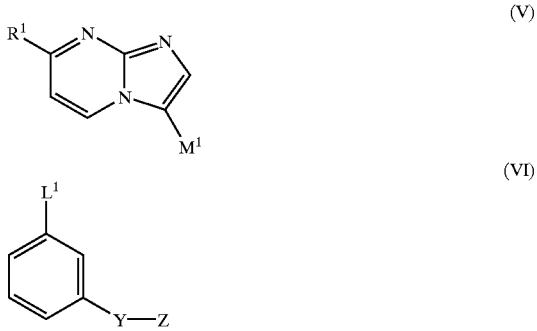

wherein Y, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents a chemical bond may be prepared by a process which comprises reacting a compound of formula VII with a compound of formula VIII:

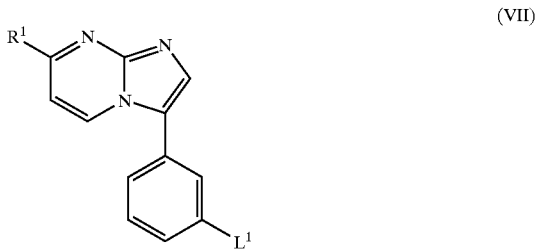

wherein Z, $R^1$, $L^1$ and $M^1$ are as defined above; in the presence of a transition metal catalyst; under conditions analogous to those described above for the reaction between compounds III and IV.

In the compounds of formula VII above, the leaving group $L^1$ is typically trifluoromethanesulfonyloxy (triilyloxy); or a halogen atom, e.g. bromo.

Alternatively, the compounds according to the present invention in which Y represents a chemical bond may be prepared by a process which comprises reacting a compound of formula IX with a compound of formula X:

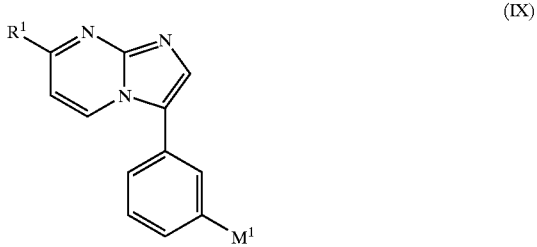

wherein Z, $R^1$, $L^1$ and $M^1$ are as defined above; in the presence of a transition metal catalyst; under conditions analogous to those described above for the reaction between compounds III and IV.

In an additional procedure, the compounds according to the present invention in which Y represents an oxygen atom may be prepared by a process which comprises reacting a compound of formula X as defined above with a compound of formula XI:

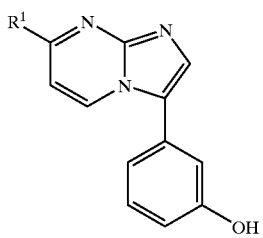
(XI)

wherein $R^1$ is as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

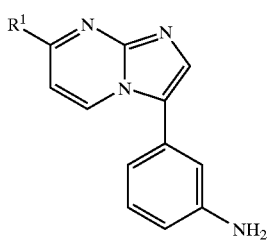
(XII)

wherein $R^1$ is as defined above.

In relation to the reaction between compounds X and XII, the leaving group $L^1$ in the compounds of formula X may suitably represent fluoro.

The reaction between compounds X and XII is conveniently carried out by heating the reactants, typically at a temperature in the region of 120° C., in a solvent such as N,N-dimethylformamide.

Where $M^1$ in the intermediates of formula IV and IX above represents a cyclic ester of a boronic acid moiety —B(OH)$_2$ formed with pinacol or neopentyl glycol, the relevant compound IV or IX may be prepared by reacting bis(pinacolato)diboron or bis(neopentyl glycolato)diborane respectively with a compound of formula VIA or VIIA:

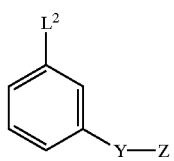
(VIA)

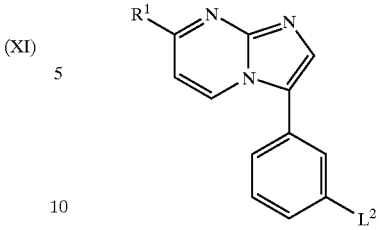
(VIIA)

wherein Y, Z and $R^1$ are as defined above, and $L^2$ represents hydroxy or a suitable leaving group; in the presence of a transition metal catalyst.

Where $L^2$ represents a leaving group, this is typically triflyloxy; or a halogen atom such as bromo.

The transition metal catalyst of use in the reaction between bis(pinacolato)diboron or bis(neopentyl glycolato) diborane and compound VIA or VIIA is suitably dichloro [1,1'-bis(diphenylphosphino)ferrocene]-palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where $L^1/L^2$ in the intermediates of formula VII/VIIA above represents triflyloxy, the relevant compound VII/VIIA may be prepared by reacting the appropriate compound of formula XI as defined above with triflic anhydride, typically in the presence of pyridine. Analogous conditions may be utilised for converting an intermediate of formula VIA above wherein $L^2$ represents hydroxy into the corresponding compound of formula VI/VIA wherein $L^1/L^2$ represents triflyloxy.

The intermediates of formula XI above may suitably be prepared from the appropriate methoxy-substituted precursor of formula XIII:

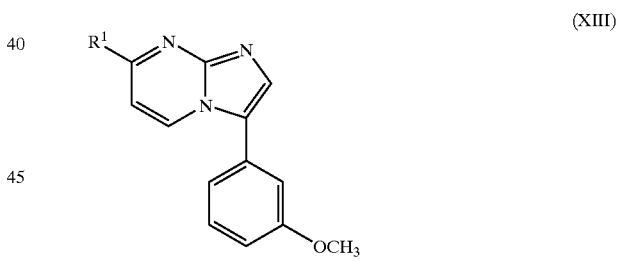
(XIII)

wherein $R^1$ is as defined above; by treatment with hydrogen bromide, typically in acetic acid at reflux.

The intermediates of formula XII and XIII above may be prepared by reacting a compound of formula III as defined above with the appropriate compound of formula XV:

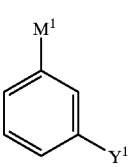
(XIV)

wherein $M^1$ is as defined above, and $Y^1$ represents amino or methoxy; in the presence of a transition metal catalyst; under conditions analogous to those described above for the reaction between compounds III and IV. In particular, the transition metal catalyst of use in the reaction between compounds III and XIV is suitably tetrakis(triphenylphosphine)-palladium(0), in which case the reaction is conveniently carried out at an elevated temperature in a solvent such as aqueous 1,2-dimethoxyethane, advantageously in the presence of sodium carbonate.

Where M¹ in the intermediates of formula V above represents —Sn(Alk)₃ and Alk is as defined above, this compound may be prepared by reacting a compound of formula III as defined above with a reagent of formula (Alk)₃Sn—Hal, in which Hal represents a halogen atom, typically chloro. The reaction is conveniently effected by treating compound III with isopropylmagnesium chloride, typically in a solvent such as tetrahydrofuran, with subsequent addition of the stannyl reagent (Alk)₃Sn—Hal.

Where L¹ in the intermediates of formula III above represents bromo, this compound may be prepared by bromination of the corresponding compound of formula XV:

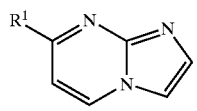

(XV)

wherein R¹ is as defined above; typically by treatment with bromine in methanol, in the presence of sodium acetate and optionally also potassium bromide.

The intermediates of formula XV may be prepared by reacting chloroacetaldehyde or bromoacetaldehyde, or an acetal derivative thereof, e.g. the dimethyl or diethyl acetal thereof, with the requisite compound of formula XVI:

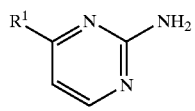

(XVI)

wherein R¹ is as defined above.

Where chloroacetaldehyde or bromoacetaldehyde is utilised as one of the reactants, the reaction is conveniently carried out by heating the reactants under basic conditions in a suitable solvent, e.g. sodium methoxide or sodium hydrogencarbonate in a lower alkanol such as methanol and/or ethanol at the reflux temperature of the solvent. Where an acetal derivative of chloroacetaldehyde or bromoacetaldehyde, e.g. the dimethyl or diethyl acetal thereof, is utilised as one of the reactants, the reaction is conveniently effected by heating the reactants under acidic conditions in a suitable solvent, e.g. aqueous hydrobromic acid in a lower alkanol such as methanol or ethanol, typically at the reflux temperature of the solvent.

In a still further procedure, the compounds according to the present invention may be prepared by a process which comprises reacting a compound of formula XVI as defined above with a compound of formula XVII:

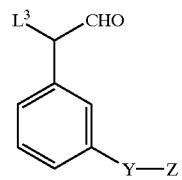

(XVII)

wherein Y and Z are as defined above, and L³ represents a suitable leaving group; under conditions analogous to those described above for the reaction between chloroacetaldehyde or bromoacetaldehyde, or an acetal derivative thereof, and compound XVI.

The leaving group L³ is suitably a halogen atom, e.g. bromo.

The intermediates of formula XV may also be prepared by reacting a compound of formula XVIII or XIX with the compound of formula XX, or with an acid addition salt of the latter compound, e.g. the hemnisulfate salt:

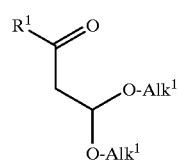

(XVIII)

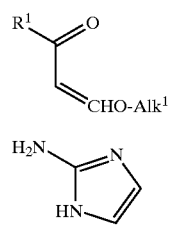

(XIX)

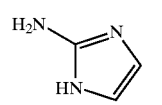

(XX)

wherein R¹ is as defined above, and Alk¹ represents C₁₋₆ alkyl.

Typical values of Alk¹ include methyl and ethyl.

The reaction is conveniently effected by heating the reactants under basic conditions in a suitable solvent, e.g. a lower alkoxide such as sodium methoxide or ethoxide in a lower alkanol such as methanol or ethanol, typically at the reflux temperature of the solvent.

In a yet further procedure, the compounds according to the present invention wherein R¹ represents an aryl or heteroaryl moiety may be prepared by a process which comprises reacting a compound of formula XXI with a compound of formula XXII:

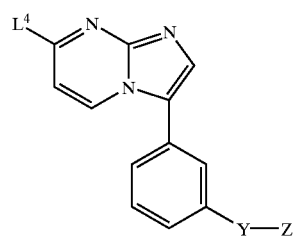

(XXII)

wherein Y, Z and M¹ are as defined above, R¹ᵃ represents an aryl or heteroaryl moiety, and L⁴ represents a suitable leaving group; in the presence of a transition metal catalyst.

The leaving group L⁴ is typically a halogen atom, e.g. chloro.

The transition metal catalyst of use in the reaction between compounds XXI and XXII is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)palladium(0), in which case the reaction is conveniently effected at an elevated temperature in a solvent such as 1,4-dioxane, typically in the presence of tri-tert-butylphosphine and cesium carbonate.

Where $L^4$ in the compounds of formula XXI above represents a halogen atom, these compounds correspond to compounds of formula I as defined above wherein $R^1$ represents halogen, and they may therefore be prepared by any of the methods described above for the preparation of the compounds according to the invention.

The compound of formula XX above is commercially available from the Sigma-Aldrich Company Ltd., Dorset, United Kingdom.

Where they are not commercially available, the starting materials of formula VI, VIII, X, XIV, XVI, XVII, XVIII, XIX and XXI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents $-C(O-Alk^1)_2R^a$ initially obtained, wherein $Alk^1$ is as defined above, may be converted into the corresponding compound of formula I wherein $R^1$ represents $-COR^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula $H_2N-OR^b$ to provide a compound of formula I wherein $R^1$ represents $-CH=NOR^b$. Furthermore, a compound of formula I wherein $R^1$ represents $-CH=NOH$ may be treated with triethylamine in the presence of 1,1'-carbonyldiimidazole to afford a corresponding compound of formula I wherein $R^1$ represents cyano. Alternatively, the compound of formula I wherein $R^1$ represents formyl may be reacted with a Grignard reagent of formula $R^aMgBr$ to afford a compound of formula I wherein $R^1$ represents $-CH(OH)R^a$, and this compound may in turn be oxidised using manganese dioxide to the corresponding compound of formula I wherein $R^1$ represents $-COR^a$. The latter compound may then be condensed with a hydroxylamine derivative of formula $H_2N-OR^b$ to provide a compound of formula I wherein $R^1$ represents $-CR^a=NOR^b$. A compound of formula I wherein $R^1$ represents $-CH(OH)R^a$ may be converted into the corresponding compound of formula I wherein $R^1$ represents $-CHFR^a$ by treatment with (diethylamino)sulfur trifluoride (DAST). Similarly, a compound of formula I wherein $R^1$ represents $-COR^a$ may be converted into the corresponding compound of formula I wherein $R^1$ represents $-CF_2R^a$ by treatment with DAST. A compound of formula I wherein $R^1$ represents amino may be converted into the corresponding compound of formula I wherein $R^1$ represents chloro by diazotisation, using sodium nitrite, followed by treatment with copper(I) chloride. A compound of formula I wherein $R^1$ represents $-COCH_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl)methyl isocyanide (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically in situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 and/or α3 and/or α5 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human $GABA_A$ receptor of 100 nM or less.

EXAMPLE 1

3'-(7-Methylimidazo[1,2-a]pyrimidin-3-yl)biphenyl-2-carbonitrile

A mixture of 2-bromobenzonitrile (9.1 g, 50 mmol), 3-aminobenzeneboronic acid monohydrate (11.6 g, 75 mmol), and tetrakis(triphenylphosphine)palladium(0) (1.73 g, 1.5 mmol) in 1,2-dimethoxyethane (50 ml) and 2M sodium carbonate solution (25 ml) was heated at 80° C. for 20 h. After cooling to ambient temperature the reaction was partitioned between ethyl acetate (400 ml) and water (400 ml). The organics were washed with brine (400 ml), dried over anhydrous sodium sulfate, filtered and concentrated in vacuo. Purification of the residue by chromatography on silica gel, eluting with isohexane on a gradient of ethyl acetate (0–25%) gave 3'-aminobiphenyl-2-carbonitrile as a colourless oil that solidified on standing to afford a white solid (9.5 g, 98%): $δ_H$ (400 MHz, $CDCl_3$) 3.79 (2H, br), 6.75 (1H, ddd, J 8, 3 and 1), 6.84 (1H, dd, J 3 and 3), 6.92 (1H, dd, J 8 and 3), 7.25 (1H, dd, J 8 and 8), 7.40 (1H, ddd, J 8, 8 and 1), 7.50 (1H, dd, J 8 and 1), 7.62 (1H, ddd, J 8, 8 and 1), 7.73 (1H, dd, J 8 and 1).

A solution of 3'-aminobiphenyl-2-carbonitrile (10.9 g, 56 mmol) in 1,4-dioxane (30 ml) was treated with a solution of 25% aqueous sulfuric acid (150 ml). The resulting suspension was cooled to 0° C. before being treated dropwise over 10 minutes with a solution of sodium nitrite (4.6 g, 67 mmol) in water (10 ml). After stirring at 0° C. for 30 minutes the reaction was poured into hot (70° C.) water (500 ml). On cooling to ambient temperature the product was extracted into ethyl acetate (500 ml), the organics were washed with water (300 ml), brine (300 ml) and dried over anhydrous sodium sulfate. Filtration and concentration in vacuo afforded 3'-hydroxybiphenyl-2-carbonitrile as a dark oil (7.1 g, 65%): $δ_H$ (400 MHz, $CDCl_3$) 5.40 (1H, br), 6.92 (1H, ddd, J 8, 3 and 1), 7.04 (1H, dd, J 3 and 3), 7.11 (1H, ddd, J 8, 3 and 1), 7.35 (1H, dd, J 8 and 8), 7.44 (1H, ddd, J 8, 8 and 1), 7.51 (1H, dd, J 8 and 1), 7.64 (1H, ddd, J 8, 8 and 1), 7.75 (1H, dd, J 8 and 1). 3'-Hydroxybiphenyl-2-carbonitrile (0.48 g, 2.47 mmol) and dry pyridine (0.98 g, 12.35 mmol) were dissolved in dichloromethane (7 ml) and cooled to 0° C. before dropwise addition of trifluoromethanesulfonic anhydride (1.04 g, 3.70 mmol) over 5 min. The mixture was stirred at 0° C. for 10 min and then at 25° C. for 1 h. The solvent was evaporated in vacuo and the residue partitioned between ethyl acetate (200 ml) and water (150 ml). The organic layer was washed with brine (150 ml), dried over anhydrous sodium sulfate and evaporated to give a brown oil. Purification by silica gel chromatography eluting with isohexane on a gradient of ethyl acetate (0–35%) gave trifluoromethanesulfonic acid 2'-cyanobiphenyl-3-yl ester as a yellow oil (544 mg, 67%): $δ_H$ (400 MHz, $CDCl_3$) 7.37 (1H, ddd, J 8, 3 and 1), 7.39 (1H, dd, J 3 and 3), 7.50–7.60 (2H, m), 7.61–7.65 (2H, m), 7.64 (1H, td, J 8 and 1), 7.80 (1H, dd, J 8 and 1).

Trifluoromethanesulfonic acid 2'-cyanobiphenyl-3-yl ester (0.55 g, 1.66 mmol), potassium acetate (0.49 g, 4.98 mmol) and bis(pinacolato)diboron (0.55 g, 2.16 mmol) were dissolved in 1,4-dioxane (10 ml) and the mixture degassed with $N_2$ for 15 min. Dichloro[1,1'-bis(diphenylphosphino)ferrocene]palladium(II) dichloromethane adduct (41 mg, 0.05 mmol) and 1,1'-bis(diphenylphosphino)ferrocene (28 mg, 0.05 mmol) were then added and the mixture heated at 85° C. for 18 h. The mixture was cooled to ambient temperature, filtered and the filter cake washed with diethyl ester. The filtrate was evaporated to dryness and partitioned between diethyl ether (25 ml) and 1N sodium hydroxide solution (25 ml). The aqueous layer was washed with more diethyl ether then made acidic (pH 6) with 4N hydrochloric acid. The resulting solid was collected by filtration and dried in vacuo to give 3'-(4,4,5,5-tetramethyl-[1,3,2]dioxaborolan-2-yl)biphenyl-2-carbonitrile as a cream-coloured solid (430 mg, 85%): $δ_H$ (400 MHz, $CDCl_3$) 1.36 (12H, s), 7.43 (1H, ddd, J 8, 8 and 1.5), 7.48–7.57 (2H, m), 7.62 (2H, ddd, J 8, 8 and 1.5), 7.68–7.71 (1H, m), 7.74–7.77 (1H, m), 7.87–7.90 (1H, m), 7.92–7.94 (1H, m).

Sodium methoxide (1.62 g, 30 mmol) was added to a stirred solution of 2-aminoimidazole hemisulfate (2.64 g, 20 mmol) and 1,1-dimethoxy-3-butanone (2 ml) in ethanol (25 ml). The mixture was heated under reflux for 8 h, allowed to cool to room temperature then pre-adsorbed directly onto silica. Purification by silica gel chromatography eluting with dichloromethane and 1% conc. ammonia on a gradient of methanol (1–4%) gave a 95:5 mixture of 7-methylimidazo[1,2-a]pyrimidine and 5-methylimidazo[1,2-a]pyrimidine respectively (1.68 g, 64%) as a white crystalline solid: $\delta_H$ (400 MHz, CDCl$_3$, 7-methyl isomer) 2.64 (3H, s), 6.74 (1H, d, J 7), 7.45 (1H, d, J 1), 7.73 (1H, d, J 1), 8.29 (1H, d, J 7).

7-Methylimidazo[1,2-a]pyrimidine (100 mg, 0.75 mmol) and sodium acetate (74 mg, 0.90 mmol) were dissolved in methanol (2 ml) which had been saturated with potassium bromide and this mixture was cooled to −10° C. before dropwise addition of bromine (132 mg, 0.83 mmol) over 5 min. On complete addition the mixture was quenched by addition of 1M sodium sulfite solution (2 ml) and the solvent removed in vacuo. The residue was treated with water (15 ml) and saturated sodium hydrogencarbonate solution (15 ml) and extracted with ethyl acetate (3×40 ml). The organics were combined then washed with brine (40 ml), dried over anhydrous sodium sulfate and evaporated to give an off white solid. This solid was purified by silica gel chromatography eluting with dichloromethane and 1% conc. ammonia on a gradient of methanol (1–2%) to give 3-bromo-7-methylimidazo[1,2-a]pyrimidine (100 mg, 63%) as a white crystalline solid: $\delta_H$ (400 MHz, CDCl$_3$) 2.67 (3H, s), 6.87 (1H, d, J 7), 7.71 (1H, s), 8.27 (1H, d, J 7).

3-Bromo-7-methylimidazo[1,2-a]pyrimidine (100 mg, 0.47 mmol), potassium phosphate (200 mg, 0.94 mmol) and 3'-(4,4,5,5-tetramethyl-[1,3,2]dioxaborolan-2-yl)biphenyl-2-carbonitrile (215 mg, 0.70 mmol) were dissolved in N,N-dimethylacetamide (2 ml) and the mixture degassed with N$_2$ for 15 min. Tetrakis(triphenylphosphine)palladium(0) (27 mg, 0.002 mmol) was added and the mixture heated at 65° C. for 24 h. The mixture was allowed to cool to room temperature, diluted with water (20 ml) and saturated sodium hydrogencarbonate solution (20 ml) then extracted with ethyl acetate (2×75 ml). The combined organic fractions were washed with brine (40 ml), dried over anhydrous sodium sulfate and evaporated to give a black oil. The oil was purified by silica gel chromatography eluting with dichloromethane and 1% conc. ammonia on a gradient of methanol (1–2%). The solid obtained was triturated with diethyl ether to furnish 3'-(7-methylimidazo[1,2-a]pyrimidin-3-yl)biphenyl-2-carbonitrile (120 mg, 82%) as a white powder: $\delta_H$ (400 MHz, CDCl$_3$) 2.67 (3H, s), 6.83 (1H, d, J 7), 7.49 (1H, td, J 8 and 1), 7.55–7.75 (6H, m), 7.82 (1H, dd, J 8 and 1), 7.85 (1H, s), 8.82 (1H, d, J 7).

EXAMPLE 2

3'-(Imidazo[1,2-a]pyrimidin-3-yl)biphenyl-2-carbonitrile

A solution of 2-aminopyrimidine (0.5 g, 5.26 mmol), bromoacetaldehyde diethyl acetal (2.07 g, 10.5 mmol) and 48% aqueous hydrobromic acid (0.5 ml) in ethanol (5 ml) was heated at reflux for 18 h. The reaction was cooled and pre-adsorbed directly onto silica gel. Purification by flash chromatography eluting with dichloromethane (containing 1% conc. ammonia) on a gradient of methanol (1–3%) gave a solid which was triturated with 5% diethyl ether in isohexane to afford imidazo[1,2-a]pyrimidine (0.51 g, 82%) as a tan solid: $\delta_H$ (400 MHz, CDCl$_3$) 6.92 (1H, dd, J 7 and 4), 7.59 (1H, d, J 1), 7.84 (1H, d, J 1), 8.49 (1H, dd, J 7 and 2), 8.58 (1H, dd, J 7 and 2).

Imidazo[1,2-a]pyrimidine (0.20 g, 1.68 mmol) was brominated as described in Example 1 to give 3-bromoimidazo[1,2-a]pyrimidine (0.29 g, 87%) as a white solid: $\delta_H$ (400 MHz, CDCl$_3$) 7.02 (1H, dd, J 7 and 4), 7.83 (1H, s), 8.43 (1H, dd, J 7 and 2), 8.59 (1H, dd, J 7 and 2).

3-Bromoimidazo[1,2-a]pyrimidine (0.29 g, 1.68 mmol) was coupled with 3'-(4,4,5,5-tetramethyl-[1,3,2]dioxaborolan-2-yl)biphenyl-2-carbonitrile as described in Example 1 to give 3'-(imidazo[1,2-a]pyrimidin-3-yl)biphenyl-2-carbonitrile (260 mg, 60%) as an off-white powder: $\delta_H$ (360 MHz, CDCl$_3$) 6.97 (1H, dd, J 7 and 4), 7.51 (1H, td, J 1 and 8), 7.59 (1H, dd, J 7 and 1), 7.62–7.73 (4H, m), 7.77–7.78 (1H, m), 7.82 (1H, dd, J 8 and 1), 7.96 (1H, s), 8.60 (1H, dd, J 7 and 2), 8.98 (1H, d, J 7 and 2); m/z (ES$^+$) 297 (M$^+$+H).

EXAMPLE 3

3'-(7-Trifluoromethylimidazo[1,2-a]pyrimidin-3-yl)biphenyl-2-carbonitrile

A mixture of 2-amino-4-(trifluoromethyl)pyrimidine (prepared according to Zanatta et al. in *J. Heterocyclic Chem.*, 1997, 34(2), 509–513) (500 mg, 3.1 mmol) and bromoacetaldehyde diethyl acetal (1.38 ml, 9.2 mmol) in ethanol (10 ml) was treated with hydrobromic acid (0.5 ml of a 48% aqueous solution) and then heated at 70° C. for 12 h. The reaction was cooled to ambient temperature then pre-adsorbed onto silica. Purification by chromatography on silica eluting with dichloromethane (containing 1% conc. ammonia) on a gradient of methanol (1–5%) afforded 7-trifluoromethylimidazo[1,2-a]pyrimidine (500 mg, 87%) as a cream-coloured solid: $\delta_H$ (400 MHz, CDCl$_3$) 7.22 (1H, d, J 7), 7.74 (1H, d, J 1), 8.03 (1H, d, J 1), 8.67 (1H, d, J 7).

7-Trifluoromethylimidazo[1,2-a]pyrimidine (0.20 g, 1.07 mmol) was brominated as described in Example 1 to give 3-bromo-7-trifluoromethylimidazo[1,2-a]pyrimidine (0.28 g, 98%) as a white solid: $\delta_H$ (400 MHz, CDCl$_3$) 7.35 (1H, d, J 7), 8.02 (1H, s), 8.62 (1H, d, J 7).

3-Bromo-7-trifluoromethylimidazo[1,2-a]pyrimidine (0.28 g, 1.04 mmol) was coupled with 3'-(4,4,5,5-tetramethyl-[1,3,2]dioxaborolan-2-yl)biphenyl-2-carbonitrile as described in Example 1 to give 3'-(7-trifluoromethylimidazo[1,2-a]pyrimidin-3-yl)biphenyl-2-carbonitrile (165 mg, 44%) as a yellow powder: $\delta_H$ (400 MHz, CDCl$_3$) 7.29 (1H, d, J 7), 7.53 (1H, td, J 8 and 1), 7.59–7.68 (3H, m), 7.70–7.75 (2H, m), 7.80–7.85 (2H, m), 8.14 (1H, s), 9.20 (1H, d, J 7); m/z (ES$^+$) 365 (M$^+$+H).

EXAMPLE 4

3'-[7-(1,1-Dimethoxyethyl)imidazo[1,2-a]pyrimidin-3-yl]biphenyl-2-carbonitrile

Boron trifluoride etherate (17.03 g, 120.0 mmol) was added dropwise over 15 min to a cooled (−40° C.) solution of triethyl orthoformate (14.82 g, 100.0 mmol) in dichloromethane (50 ml). Stirring was continued for 10 min then the solution was transferred to an ice-water bath and stirred at 0° C. for 20 min. The mixture was cooled to −78° C., and 3,3-dimethoxy-2-butanone (6.61 g, 50.0 mmol) added followed by dropwise addition of N,N-diisopropylethylamine (19.39 g, 150.0 mmol) over 15 min. Stirring was continued for 1 h then the solution was poured onto a vigorously stirred mixture of saturated sodium hydrogencarbonate solution (500 ml) and dichloromethane (200 ml). The organic phase was separated, washed with ice-cold 1M sulfuric acid solution (2×500 ml) and ice-cold water (2×500 ml), dried over anhydrous sodium sulfate solution and evaporated to give 1,1-diethoxy-4,4-dimethoxypentan-3-one (11.72 g, 100%) as an orange oil.

1,1-Diethoxy-4,4-dimethoxypentan-3-one was condensed with 2-aminoimidazole hemisulfate as described in Example 1 to give 7-(1,1-dimethoxyethyl)imidazo[1,2-a]pyrimidine (6.61 g, 64%) as a white solid: $\delta_H$ (400 MHz, CDCl$_3$) 1.70 (3H, s), 3.28 (6H, s), 7.30 (1H, d, J 7), 7.55 (1H, d, J 1), 7.84 (1H, d, J 1), 8.43 (1H, d, J 7).

7-(1,1-Dimethoxyethyl)imidazo[1,2-a]pyrimiidine (207 mg, 1.00 mmol) was brominated as described in Example 1 to give 3-bromo-7-(1,1-dimethoxyethyl)imidazo[1,2-a]pyrimidine (197 mg, 69%) as a white solid: $\delta_H$ (360 MHz, CDCl$_3$) 1.70 (3H, s), 3.28 (6H, s), 7.43 (1H, d, J 7), 7.82 (1H, s), 8.39 (1H, d, J 7).

3-Bromo-7-(1,1-dimethoxyethyl)imidazo[1,2-a]pyrimidine (197 mg, 0.50 mmol) was coupled with 3'-(4,4,5,5-tetramethyl-[1,3,2]dioxaborolan-2-yl)biphenyl-2-carbonitrile as described in Example 1 to give 3'-[7-(1,1-dimethoxyethyl)imidazo[1,2-a]pyrimidin-3-yl]biphenyl-2-carbonitrile (200 mg, 76%) as a white powder: $\delta_H$ (360 MHz, CDCl$_3$) 1.72 (3H, s), 3.30 (6H, s), 7.39 (1H, d, J 7), 7.49–7.73 (6H, m), 7.78–7.84 (2H, m), 7.97 (1H, s), 8.95 (1H, d, J 7); m/z (ES$^+$) 385 (M$^+$+H).

EXAMPLE 5

3'-(7-Acetyliyidazo[1,2-a]pyrimidin-3-yl)biphenyl-2-carbonitrile

A solution of 3'-[7-(1,1-dimethoxyethyl)imidazo[1,2-a]pyrimidin-3-yl]biphenyl-2-carbonitrile (100 mg, 0.26 mmol) in 2.5N hydrochloric acid (4 ml) was heated at 50° C. for 15 h. The mixture was cooled, layered with ethyl acetate (5 ml) and made basic (pH 8) with portionwise addition of solid sodium hydrogencarbonate over 15 min. The mixture was diluted with water (5 ml) and extracted with dicliloromethane (5×30 ml). The combined organics were dried over anhydrous sodium sulfate, filtered, evaporated to dryness and triturated with diethyl ether to give 3'-(7-acetylimidazo[1,2-a]pyrimnidin-3-yl)biphenyl-2-carbonitrile (62 mg, 70%) as a yellow solid: $\delta_H$ (360 MHz, CDCl$_3$) 2.84 (3H, s), 7.26 (1H, d, J 7), 7.52 (1H, td, J 8 and 1), 7.58–7.72 (5H, m), 7.80–7.84 (2H, m), 8.16 (1H, s), 9.03 (1H, d, J 7); m/z (ES$^+$) 339 (M$^+$+H).

EXAMPLE 6

3'-(7-Isopropylimidazo[1,2-a]pyrimidin-3-yl)biphenyl-2-carbonitrile

3-Methylbutan-2-one was converted to 1,1-diethoxy-4-methylpentan-3-one as described in Example 4 and condensed with 2-aminoimidazole hemisulfate as described in Example 1 to give 7-isopropylimidazo[1,2-a]pyrimidine as an orange solid: $\delta_H$ (400 MHz, CDCl$_3$) 1.36 (6H, d, J 7), 3.12 (1H, septet, J 7), 6.78 (1H, d, J 7), 7.45 (1H, d, J 1), 7.72 (1H, d, J 1), 8.33 (1H, d, J 7).

7-Isopropylimidazo[1,2-a]pyrimidine was brominated as described in Example 1 to give 3-bromo-7-isopropylimidazo[1,2-a]pyrimidine as a cream-coloured solid: $\delta_H$ (400 MHz, CDCl$_3$) 1.37 (6H, d, J 7), 3.16 (1H, septet, J 7), 6.91 (1H, d, J 7), 7.71 (1H, s), 8.30 (1H, d, J 7).

3-Bromo-7-isopropylimidazo[1,2-a]pyrimidine was coupled with 3'-(4,4,5,5-tetramethyl-[1,3,2]dioxaborolan-2-yl)biphenyl-2-carbonitrile as described in Example 1 to give 3'-(7-isopropylimidazo[1,2-a]pyrimidin-3-yl)biphenyl-2-carbonitrile as a white powder: Found C, 76.71; H, 5.17; N 16.24. $C_{22}H_{18}N_4.0.3(H_2O)$ requires C, 76.59; H, 5.43; N, 16.24; $\delta_H$ (400 MHz, CDCl$_3$) 1.38 (6H, d, J 7), 3.16 (1H, septet, J 7), 6.88 (1H, d, J 7), 7.48–7.76 (7H, m), 7.82 (1H, dd, J 8 and 1), 7.85 (1H, s), 8.85 (1H, d, J 7); m/z (ES$^+$) 339 (M$^+$+H).

EXAMPLE 7

3'-(7-Cyclopropylimidazo[1,2-a]pyrimidin-3-yl)biphenyl-2-carbonitrile

Cyclopropyl methyl ketone was converted to 1-cyclopropyl-3,3-diethoxypropan-1-one as described in Example 4 and condensed with 2-aminoimidazole hemisulfate as described in Example 1 to give 7-cyclopropylimidazo[1,2-a]pyrimidine as an orange solid: $\delta_H$ (400 MHz, CDCl$_3$) 1.06–1.11 (2H, m), 1.26–1.31 (2H, m), 2.03–2.08 (1H, m), 6.74 (1H, d, J 7), 7.40 (1H, d, J 1), 7.65 (1H, d, J 1), 8.24 (1H, d, J 7).

7-Cyclopropyhimidazo[1,2-a]pyrimidine was brorninated as described in Example 1 to give 3-bromo-7-cyclopropylimidazo[1,2-a]pyrimidine as a tan solid: $\delta_H$ (400 MHz, CDCl$_3$) 1.10–1.15 (2H, m), 1.29–1.32 (2H, m), 2.04–2.12 (1H, m), 6.88 (1H, d, J 7), 7.63 (1H, s), 8.20 (1H, d, J 7).

3-Bromo-7-cyclopropylimidazo[1,2-a]pyrimidine was coupled with 3'-(4,4,5,5-tetramethyl-[1,3,2]dioxaborolan-2-yl)biphenyl-2-carbonitrile as described in Example 1 to give 3'-(7-cyclopropylimidazo[1,2-a]pyrimidin-3-yl)biphenyl-2-carbonitrile. Hydrochloride salt, white powder (from acetonitrile): $\delta_H$ (400 MHz, DMSO) 1.21–1.25 (2H, m), 1.31–1.36 (2H, m), 2.46–2.52 (1H, m), 7.58 (1H, d, J 7), 7.65 (1H, td, J 7 and 1), 7.77–7.88 (5H, m), 7.93–7.94 (1H, m), 8.01 (1H, dd, J 7 and 1), 8.37 (1H, s), 9.16 (1H, d, J 7); m/z (ES$^+$) 337 (M$^+$+H).

EXAMPLE 8

3'-(7-tert-Butylimidazo[1,2-a]pyrimidin-3-yl)biphenyl-2-carbonitrile 3,3-Dimethylbutan-2-one was converted to 1,1-diethoxy-4,4-dimethylpentan-3-one as described in Example 4 and condensed with 2-aminoimidazole hemisulfate as described in Example 1 to give 7-tert-butylimidazo[1,2-a]pyrimidine as a pale-orange solid: $\delta_H$ (400 MHz, CDCl$_3$) 1.42 (9H, s), 6.96 (1H, d, J 7), 7.45 (1H, d, J 1), 7.72 (1H, d, J 1), 8.33 (1H, d, J 7).

7-tert-Butylimidazo[1,2-a]pyrimidine was brominated as described in Example 1 to give 3-bromo-7-tert-butylimidazo[1,2-a]pyrimidine as an off-white solid: $\delta_H$ (400 MHz, CDCl$_3$) 1.43 (9H, s), 7.09 (1H, d, J 7), 7.71 (1H, s), 8.30 (1H, d, J 7).

3-Bromo-7-tert-butylimidazo[1,2-a]pyrimidine was coupled with 3'-(4,4,5,5-tetramethyl-[1,3,2]dioxaborolan-2-yl)biphenyl-2-carbonitrile as described in Example 1 to give 3'-(7-tert-butylimidazo[1,2-a]pyrimidin-3-yl)biphenyl-2-carbonitrile as an off-white powder: Found C, 77.17; H, 5.79; N, 15.78. $C_{23}H_{20}N_4.0.3(H_2O)$ requires C, 77.21; H, 5.80; N, 15.66; $\delta_H$ (400 MHz, CDCl$_3$) 1.44 (9H, s), 7.05 (1H, d, J 7), 7.48–7.76 (7H, m), 7.83 (1H, dd, J 8 and 1), 7.86 (1H, s), 8.88 (1H, d, J 7); m/z (ES$^+$) 353 (M$^+$+H).

EXAMPLE 9

3'-(7-Cyclobutylimidazo[1,2-a]pyrimidin-3-yl)biphenyl-2-carbonitrile

Cyclobutyl methyl ketone was converted to 1-cyclobutyl-3,3-diethoxypropan-1-one as described in Example 4 and condensed with 2-aminoimidazole hemisulfate as described in Example 1 to give 7-cyclobutylimidazo[1,2-a]pyrimidine as an orange solid: $\delta_H$ (400 MHz, CDCl$_3$) 1.90–2.55 (6H, m), 3.71 (1H, quintet, J 8), 6.73 (1H, d, J 7), 7.45 (1H, d, J 1), 7.72 (1H, d, J 1), 8.30 (1H, dd, J 7 and 3).

7-Cyclobutylimidazo[1,2-a]pyrimidine was brominated as described in Example 1 to give 3-bromo-7-cyclobutylimidazo[1,2-a]pyrimidine as a cream-coloured solid: $\delta_H$ (400 MHz, CDCl$_3$) 1.90–2.55 (6H, m), 3.74 (1H, quintet, J 8), 6.85 (1H, d, J 7), 7.71 (1H, s), 8.27 (1H, d, J 7).

3-Bromo-7-cyclobutylimidazo[1,2-a]pyrimidine was coupled with 3'-(4,4,5,5-tetramethyl-[1,3,2]dioxaborolan-2-yl)biphenyl-2-carbonitrile as described in Example 1 to give 3'-(7-cyclobutylimidazo[1,2-a]pyrimidin-3-yl)biphenyl-2-carbonitrile as a white powder: $\delta_H$ (400 MHz, CDCl$_3$) 1.90–2.55 (6H, m), 3.77 (1H, quintet, J 8), 6.83 (1H, d, J 7), 7.48–7.75 (7H, m), 7.82 (1H, dd, J 8 and 1), 7.86 (1H, s), 8.85 (1H, d, J 7); m/z (ES$^+$) 351 (M$^+$+H).

EXAMPLE 10

3'-(7-Methoxyimidazo[1,2-a]pyrimidin-3-yl)biphenyl-2-carbonitrile

2-Amino-4-chloropyrimidine (1.00 g, 7.72 mmol) and sodium methoxide (1.25 g, 23.2 mmol) were suspended in methanol (20 ml) and heated under reflux for 2 h then cooled to ambient temperature. Chloroacetaldehyde (2.4 ml of a 45% w/w solution in water, 15.44 mmol) was added and the mixture heated under reflux for 22 h, allowed to cool to ambient temperature then pre-adsorbed directly onto silica. Purification by chromatography on silica gel eluting with dichloromethane (containing 1% conc. ammonia) on a gradient of methanol (1–4%) gave 7-methoxyimidazo[1,2-a]pyrimidine (0.77 g, 67%) as a white crystalline solid: $\delta_H$ (400 MHz, CDCl$_3$) 4.04 (3H, s), 6.41 (1H, d, J 7), 7.31 (1H, d, J 1), 7.50 (1H, d, J 1), 8.17 (1H, d, J 7).

7-Methoxyimidazo[1,2-a]pyrimidine (0.66 g, 4.43 mmol) was brominated as described in Example 1 to give 3-bromo-7-methoxyimidazo[1,2-a]pyrimidine (0.48 g, 48%) as an off-white solid: $\delta_H$ (360 MHz, CDCl$_3$) 4.06 (3H, s), 6.53 (1H, d, J 7), 7.48 (1H, s), 8.14 (1H, 7).

3-Bromo-7-methoxyimidazo[1,2-a]pyrimidine (0.48 g, 2.12 mmol) was coupled with 3'-(4,4,5,5-tetramethyl-[1,3,2]dioxaborolan-2-yl)biphenyl-2-carbonitrile as described in Example 1 to give 3'-(7-methoxyimidazo[1,2-a]pyrimidin-3-yl)biphenyl-2-carbonitrile (458 mg, 66%) as a white powder: $\delta_H$ (400 MHz, CDCl$_3$) 4.08 (3H, s), 6.49 (1H, d, J 7), 7.50 (1H, td, J 8 and 1), 7.51–7.71 (8H, m), 7.81 (1H, dd, J 8 and 1), 8.66 (1H, d, J 7); m/z (ES$^+$) 327 (M$^+$+H).

EXAMPLE 11

3'-(7-Hydroxymethylimidazo[1,2-a]pyrimidin-3-yl)biphenyl-2-carbonitrile

Pyruvic aldehyde dimethyl acetal (8.43 g, 71.4 mmol) and N,N-dimethylformamide dimethyl acetal (8.51 g, 71.4 mmol) were heated at 100° C. for 18 h. The mixture was concentrated to give a brown oil and was then added dropwise over 10 min to a warm (60° C.) suspension of 2-aminoimidazole hemisulfate (9.43 g, 71.4 mmol) in water (50 ml). The mixture was heated at 50° C. for 36 h, cooled to ambient temperature and then pre-adsorbed directly onto silica. Purification by chromatography on silica gel eluting with dichloromethane (containing 1% conc. ammonia) on a gradient of methanol (1–2%) gave a 3:1 mixture of 7-dimethoxymethylimidazo[1,2-a]pyrimidine and 5-dimethoxymethylimidazo[1,2-a]pyrimidine respectively. Crystallisation from toluene gave 7-dimethoxymethylimidazo[1,2-a]pyrimidine (2.20 g, 16%) as a brown crystalline solid: $\delta_H$ (400 MHz, CDCl$_3$) 3.50 (6H, s), 5.26 (1H, s), 7.15 (1H, d, J 7), 7.56 (1H, d, J 1), 7.84 (1H, d, J 1), 8.47 (1H, d, J 7).

7-Dimethoxymethylimidazo[1,2-a]pyrimidine (1.00 g, 5.18 mmol) was dissolved in 3N hydrochloric acid and heated at 48° C. for 14 h. The solution was layered with ethyl acetate (30 ml) and solid sodium hydrogencarbonate (1.06 g, 12.6 mmol) was added in portions over 5 min. The mixture was diluted with water (6 ml) and extracted with dichloromethane (5×50 ml). The combined organics were dried over anhydrous sodium sulfate, filtered and evaporated to give imidazo[1,2-a]pyrimidine-7-carbaldehyde (749 mg, 99%) as a yellow solid: $\delta_H$ (360 MHz, CDCl$_3$) 7.53 (1H, d, J 7), 7.77 (1H, d, J 1), 8.10 (1H, d, J 1), 8.60 (1H, d, J 7), 10.05 (1H, s).

Sodium triacetoxyborohydride (21.5 g, 102 mmol) was added portionwise over 20 min to a stirred solution of imidazo[1,2-a]pyrimidine-7-carbaldehyde (5.00 g, 34.0 mmol) in methanol (100 ml) and the solution left to stir at ambient temperature for 18 h. The solvent was evaporated, the residue redissolved in methanol (150 ml) and pre-adsorbed onto silica. Purification by chromatography on silica gel eluting with dichloromethane (containing 1% conc. ammonia) on a gradient of methanol (1–10%) gave imidazo[1,2-a]pyrimidin-7-ylmethanol (5.06 g, 99%) as a white solid: $\delta_H$ (360 MHz, DMSO) 4.57 (2H, d, J 6), 5.62 (1H, t, J 6), 7.13 (1H, d, J 7), 7.64 (1H, d, J 1), 7.86 (1H, d, J 1), 8.94 (1H, d, J 7).

Imidazo[1,2-a]pyrimidin-7-ylmethanol (1.70 g, 11.4 mmol) was brominated as described in Example 1 to give 3-bromoimidazo[1,2-a]pyrimidin-7-ylmethanol (912 mg, 35%) as a white solid: $\delta_H$ (400 MHz, CDCl$_3$) 2.95 (1H, br), 4.88 (2H, s), 7.03 (1H, d, J 7), 7.73 (1H, s), 8.37 (1H, d, J 7).

3-Bromoimidazo[1,2-a]pyrimidin-7-ylmethanol (912 mg, 4.00 mmol) was dissolved in dichloromethane (10 ml) and treated with imidazole (0.70 g, 10.3 mmol) and tert-butyldimethylsilyl chloride (0.77 g, 5.1 mmol) and the mixture left to stir at ambient temperature for 1 h. The reaction was diluted with dichloromethane (75 ml) and washed with 0.01N hydrochloric acid (2×50 ml). The organic phase was washed with saturated sodium hydrogencarbonate solution (50 ml), water (50 ml) and brine (50 ml), dried over anhydrous magnesium sulfate, filtered and evaporated to give crude 3-bromo-7-(tert-butyldimethylsilanyloxymethyl)imidazo[1,2-a]pyrimidine (1.37 g, 100%) as a yellow solid.

3-Bromo-7-(tert-butyldimethylsilanyloxymethyl)imidazo[1,2-a]pyrimidine (1.37 g, 4.00 mmol) was coupled with 3'-(4,4,5,5-tetramethyl-[1,3,2]dioxaborolan-2-yl)biphenyl-2-carbonitrile as described in Example 1 to give 3'-[7-(tert-butyldimethylsilanyloxymethyl)imidazo[1,2-a]pyrimidin-3-yl]biphenyl-2-carbonitrile as a yellow solid. This solid was suspended in methanol (25 ml) and treated with conc. hydrochloric acid (1 ml) and left to stir at ambient temperature for 5 min. The solution was loaded onto a cartridge of strong cation-exchange resin, eluting with methanol then with 10% conc. ammonia in methanol. The basic fractions were concentrated in vacuo and the residue purified further by chromatography on silica gel. Elution with dichloromethane (containing 1% conc. ammonia) on a gradient of methanol (2–5%) afforded 3'-(7-hydroxymethylimidazo[1,2-a]pyrimidin-3-yl)biphenyl-2-carbonitrile (587 mg, 45%) as a yellow powder: $\delta_H$ (400 MHz, CDCl$_3$) 1.90 (1H, s), 4.88 (2H, s), 6.91 (1H, d, J 7), 7.51 (1H, td, J 8 and 1), 7.57–7.73 (5H, m), 7.77 (1H, dd, J 1 and 1), 7.82 (1H, dd, J 8 and 1), 7.89 (1H, s), 8.94 (1H, d, J 7); m/z (ES$^+$) 327 (M$^+$+H).

EXAMPLE 12

3'-(7-Fluoromethylimidazo[1,2-a]pyrimidin-3-yl)biphenyl-2-carbonitrile

To a cooled (−78° C.) suspension of 3'-(7-hydroxymethylimidazo[1,2-a]pyrimidin-3-yl)biphenyl-2-carbonitrile (75 mg, 0.23 mmol) in dichloromethane (20 ml) was added (diethylamino)sulfur trifluoride (39 mg, 0.24 mmol) dropwise over 5 min. The mixture was stirred at −78° C. for 20 min then allowed to warm to −40° C. for 5 min before quenching the reaction with a pre-cooled (−40° C.) solution of acetic acid (0.5 ml) in dichloromethane (5 ml). The mixture was warmed to ambient temperature, made basic with saturated sodium hydrogencarbonate solution (30 ml) and extracted with dichloromethane (2×50 ml). The combined organics were washed with brine (30 ml), dried over anhydrous sodium sulfate and evaporated to dryness. Purification of this material by preparative thin-layer chromatography eluting with dichloromethane/methanol/conc. ammonia (96:4:0.4) gave a solid which was triturated with diethyl ether to give 3'-(7-fluoromethylimidazo[1,2-a]pyrimidin-3-yl)biphenyl-2-carbonitrile (8 mg, 11%) as a yellow powder: $\delta_H$ (360 MHz, CDCl$_3$) 5.57 (2H, d, J 47), 7.20 (1H, dd, J 7 and 2), 7.52 (1H, dt, J 8 and 1), 7.58–7.74 (5H, m), 7.78–7.79 (1H, m), 7.83 (1H, d, J 8), 7.95 (1H, s), 9.03 (1H, dd, J 7 and 1); m/z (ES$^+$) 329 (M$^+$+H).

EXAMPLE 13

3'-(7-Formylimidazo[2-a]pyrimidin-3-yl)biphenyl-2-carbonitrile

3'-(7-Hydroxymethylimidazo[1,2-a]pyrimidin-3-yl)biphenyl-2-carbonitrile (20 mg, 0.061 mmol) and manganese(IV) oxide (53 mg, 0.61 mmol) were suspended in 1,2-dichloroethane (2 ml) and heated at 50° C. for 18 h. The mixture was filtered through Celite and the filtrate concentrated in vacuo. Purification of the residue by preparative thin-layer chromatography eluting with dichloromethane/methanol/conc. ammonia (96:3:0.3) gave a solid which was triturated with diethyl ether to give 3'-(7-formylimidazo[1,2-a]pyrimidin-3-yl)biphenyl-2-carbonitrile (10 mg, 50%) as a yellow powder: $\delta_H$ (360 MHz, DMSO) 7.48 (1H, d, J 7), 7.64 (1H, td, J 8 and 1), 7.70–7.92 (5H, m), 7.95–8.05 (2H, m), 8.42 (1H, s), 9.32 (1H, d, J 7), 9.96 (1H, s); m/z (ES$^+$) 325 (M$^+$+H).

EXAMPLE 14

3'-(7-Hydroxyiminomethylimidazo[1,2-a]pyrimidin-3-yl)biphenyl-2-carbonitrile

3'-(7-Formylimidazo[1,2-a]pyrimidin-3-yl)biphenyl-2-carbonitrile (100 mg, 0.31 mmol) and 50% aqueous hydroxylamine (127 mg, 1.54 mmol) were dissolved in ethanol (2 ml) and the mixture heated at 40° C. for 1 h. Purification of the reaction mixture by preparative thin-layer chromatography eluting with dichloromethane/methanol/conc. ammonia (96:4:0.4) gave a solid which was triturated with diethyl ether to give 3'-(7-hydroxyiminomethylimidazo[1,2-a]pyrimidin-3-yl)biphenyl-2-carbonitrile (70 mg, 67%) as a white powder: $\delta_H$ (400 MHz, DMSO) 7.42 (1H, d, J 7), 7.61–7.80 (5H, m), 7.82–7.86 (2H, m), 7.94 (1H, dd, J 1 and 1), 8.00 (1H, dd, J 8 and 1), 8.10 (1H, d, J 8), 9.09 (1H, d, J 7), 12.20 (1H, s); m/z (ES$^+$) 340 (M$^+$+H).

EXAMPLE 15

3-(2'-Cyanobiphenyl-3-yl)imidazo[1,2-a]pyrimidine-7-carbonitrile

3'-(7-Hydroxyiminomethylimidazo[1,2-a]pyrimidin-3-yl)biphenyl-2-carbonitrile (60 mg, 0.177 mmol) and 1,1'-carbonyldiimidazole (143 mg, 0.88 mmol) were suspended in dichloromethane (2 ml) and triethylamine (89 mg, 0.88 mmol) was added dropwise over 5 min. Stirring was continued for 15 min then the mixture was heated under reflux for 90 min. Purification of the reaction mixture by preparative thin-layer chromatography eluting with dichloromethane/methanol/conc. ammonia (98:2:0.2) gave a solid which was triturated with diethyl ether to give 3-(2'-cyanobiphenyl-3-yl)imidazo[1,2-a]pyrimidine-7-carbonitrile (56 mg, 97%) as a white powder: $\delta_H$ (400 MHz, CDCl$_3$) 7.26 (1H, d, J 7), 7.53 (1H, td, J 8 and 1), 7.59–7.67 (3H, m), 7.70–7.76 (2H, m), 7.81–7.85 (2H, m), 8.24 (1H, s), 9.16 (1H, d, J 7); m/z (ES$^+$) 322 (M$^+$+H).

EXAMPLE 16

3-(2'-Methoxybiphenyl-3-yl)-7-methylimidazo[1,2-a]pyrimidine

A mixture of 3-bromo-7-methylimidazo[1,2-a]pyrimidine (5.3 g, 25 mmol), 3-methoxyphenylboronic acid (4.94 g, 32.5 mmol) and tetrakis(triphenylphosphine)palladium(0) (870 mg, 0.8 mmol) in 1,2-dimethoxyethane (40 ml) was treated with sodium carbonate (18.8 ml of a 2M aqueous solution) then heated at 85° C. for 16 h. The reaction mixture was allowed to cool to ambient temperature then partitioned between ethyl acetate and water. The organics were washed with 10% sodium carbonate solution, water, brine, dried over anhydrous magnesium sulfate, filtered then preadsorbed onto silica. Purification by chromatography on silica gel eluting with dichloromethane:conc. ammonia (99.5:0.5) on a gradient of methanol (1–3%) afforded 3-(3-methoxyphenyl)-7-methylimidazo[1,2-a]pyrimidine as a cream-coloured solid (5.3 g, 89%): $\delta_H$ (400 MHz, CDCl$_3$) 2.66 (3H, s), 3.87 (3H, s), 6.76 (1H, d, J 7), 6.95–6.98 (1H, m), 7.03–7.05 (1H, m), 7.09–7.11 (1H, m), 7.44 (1H, t, J 8), 7.80 (1H, s), 8.52 (1H, d, J 7); m/z (ES$^+$) 240 (M$^+$+H).

A mixture of 3-(3-methoxyphenyl)-7-methylimidazo[1,2-a]pyrimidine (5.02 g, 21 mmol) in hydrogen bromide (25 ml of a 30 wt. % solution in acetic acid) was heated at 130° C. for 8 h. A further portion of hydrogen bromide solution was added (25 ml) and heating continued for 16 h. The reaction was cooled to ambient temperature and diluted with ice-cold water (200 ml). The aqueous phase was made neutral with 4N sodium hydroxide then extracted with dichloromethane (2×250 ml). The organics were combined, washed with brine, dried over anhydrous magnesium sulfate, filtered and evaporated to dryness. The residue was triturated with ether to afford 3-(7-methylimidazo[1,2-a]pyrimidin-3-yl)-phenol as a light-grey solid (4.4 g, 93%): m/z (ES$^+$) 226 (M$^+$+H).

A cooled (−10° C.) suspension of 3-(7-methylimidazo[1,2-a]pyrimidin-3-yl)phenol (4.28 g, 19 mmol) in dichloromethane (75 ml) was treated with pyridine (2.46 ml, 30 mmol) then with trifluoromethanesulfonic anhydride (4.05 ml, 25 mmol) added dropwise over 15 min. The resulting dark solution was stirred at −10° C. for 30 min then warmed to ambient temperature. The reaction was diluted with dichloromethane (200 ml) then extracted with 0.1N hydrochloric acid (2×200 ml), water, brine, dried over anhydrous sodium sulfate, filtered and evaporated to dryness to afford crude trifluoromethanesulfonic acid 3-(7-methylimidazo[1,2-a]pyrimidin-3-yl)phenyl ester as a dark oil: m/z (ES$^+$) 316 (M$^+$+H). This oil was dissolved in N,N-dimethylacetamide (50 ml) and degassed with nitrogen for 30 min before adding potassium phosphate (8.1 g, 38 mmol), tetrakis(triphenylphosphine)palladium(0) (660 mg, 0.6 mmol) and 2-methoxyphenylboronic acid (4.62 g, 30.4 mmol). This reaction mixture was then heated at 80° C. for 12 h, allowed to cool to ambient temperature then partitioned between ethyl acetate and water. The organics were washed with 0.1N sodium hydroxide, water, brine, dried over anhydrous magnesium sulfate, filtered then pre-adsorbed onto silica. Purification by chromatography on silica gel eluting with dichloromethane:conc. ammonia (99.5:0.5) on a gradient of MeOH (1–4%) afforded 3-(2'-methoxybiphenyl-3-yl)-7-methylimidazo[1,2-a]pyrimidine as a pale yellow solid (4.4 g, 73%): $\delta_H$ (400 MHz, DMSO) 2.58 (3H, s), 3.82 (3H, s), 7.03–7.08 (2H, m), 7.16 (1H, d, J 8), 7.38–7.45 (2H, m), 7.53–7.65 (3H, m), 7.74 (1H, s), 7.89 (1H, s), 8.91 (1H, d, J 8); m/z (ES$^+$) 316 (M$^+$+H).

EXAMPLE 17

3-(2'-Cyanobiphenyl-3-yl)imidazo[1,2-a]pyrimidine-7-carboxylic Acid Methyl Ester 4-Ethoxy-2-oxobut-3-enoic acid methyl ester was condensed with 2-aminoimidazole hemisulfate as described in Example 1 to give imidazo[1,2-a]pyrimidine-7-carboxylic acid methyl ester as an orange solid: $\delta_H$ (400 MHz, CDCl$_3$) 4.05 (3H, s), 7.68 (1H, d, J 7), 7.72 (1H, d, J 1), 8.06 (1H, d, J 1), 8.59 (1H, d, J 7).

Imidazo[1,2-a]pyrimidine-7-carboxylic acid methyl ester was brominated as described in Example 1 to give 3-bromoimidazo[1,2-a]pyrimidine-7-carboxylic acid methyl ester as a cream-coloured solid: $\delta_H$ (400 MHz, CDCl$_3$) 4.07 (3H, s), 7.80 (1H, d, J 7), 8.04 (1H, s), 8.55 (1H, d, J 7).

3-Bromoimidazo[1,2-a]pyrimidine-7-carboxylic acid methyl ester was coupled with 3'-(4,4,5,5-tetramethyl-[1,3,2]dioxaborolan-2-yl)biphenyl-2-carbonitrile as described in Example 1 to give 3-(2'-cyanobiphenyl-3-yl)-imidazo[1,2-a]pyrimidine-7-carboxylic acid methyl ester as a pale yellow powder: $\delta_H$ (400 MHz, CDCl$_3$) 4.07 (3H, s), 7.50–7.54 (1H, m), 7.58–7.76 (6H, m), 7.81–7.84 (2H, m), 8.18 (1H, s), 9.10 (1H, d, J 7); m/z (ES$^+$) 355 (M$^+$+H).

EXAMPLE 18

3'-(7-Dimethoxymethylimidazo[1,2-a]pyrimidin-3-yl)biphenyl-2-carbonitrile

7-Dimethoxymethylimidazo[1,2-a]pyrimidine was brominated as described in Example 1 to give 3-bromo-7-dimethoxymethylimidazo[1,2-a]pyrimidine as an off-white solid: $\delta_H$ (400 MHz, CDCl$_3$) 3.50 (6H, s), 5.28 (1H, s), 7.28 (1H, d, J 7), 7.81 (1H, s), 8.43 (1H, d, J 7); m/z (ES$^+$) 272/274 (M$^+$+H).

3-Bromo-7-dimethoxyymethylimidazo[1,2-a]pyrimidine (0.28 g, 1.04 mmol) was coupled with 3'-(4,4,5,5-tetramethyl-[1,3,2]dioxaborolan-2-yl)biphenyl-2-carbonitrile as described in Example 1 to give 3'-(7-dimethoxymethylimidazo[1,2-a]pyrimidin-3-yl)biphenyl-2-carbonitrile (165 mg, 44%) as a yellow powder: $\delta_H$ (400 MHz, CDCl$_3$) 3.51 (6H, s), 5.30 (1H, s), 7.25 (1H, d, J 7), 7.51 (1H, td, J 8 and 1), 7.57–7.70 (5H, m), 7.76–7.7 (1H, m), 7.82 (1H, dd, J 8 and 1), 7.96 (1H, s), 8.97 (1H, d, J 7); m/z (ES$^+$) 371 (M$^+$+H).

EXAMPLE 19

3'-[7-([1,2,4]Triazol-1-ylmethyl)imidazo[1,2-a]pyrimidin-3-yl]biphenyl-2-carbonitrile To a solution of 3'-(7-hydroxymethylimidazo[1,2-a]pyrimidin-3-yl)-biphenyl-2-carbonitrile (0.1 g, 0.31 mmol) in dichloromethane (5 ml) was added carbon tetrabromide (153 mg, 0.46 mmol) and triphenylphosphine (121 mg, 0.46 mmol). This mixture was stirred at ambient temperature for 6 h after which time 1,2,4-triazole sodium salt (84 mg, 0.93 mmol) was added and the reaction stirred at ambient temperature for a further 18 h. The solvent was removed in vacuo and the residue purified by silica gel chromatography eluting with dichloromethane on a gradient of methanol (0–10%). Further purification by high performance liquid chromatography gave 3'-[7-([1,2,4]triazol-1-ylmethyl)imidazo[1,2-a]pyrimidin-3-yl]biphenyl-2-carbonitrile (15.3 mg): $\delta_H$ (400 MHz, DMSO) 5.76 (2H, s), 7.32 (1H, d, J 7), 7.52–7.84 (8H, m), 8.16 (2H, d, J 5), 8.73 (1H, s), 9.22 (1H, s); m/z (ES$^+$) 378 (M$^+$+H).

EXAMPLE 20

3'-(7-Difluoromethylimidazo[1,2-a]pyrimidin-3-yl)bihenyl-2-carbonitrile

4-Ethoxy-1,1-difluorobut-3-en-2-one was condensed with 2-aminoimidazole hemisulfate using the procedure described in Example 1 to give 7-difluoromethylimidazo[1,2-a]pyrimidine (16.9 g, 46%) as a pale brown crystalline solid: $\delta_H$ (400 MHz, CDCl$_3$) 6.64 (1H, t, J 55), 7.26 (1H, d, J 7), 7.67 (1H, d, J 1), 7.95 (1H, d, J 1), 8.60 (1H, d, J 7).

7-Difluoromethylimidazo[1,2-a]pyrimidine (1.00 g, 5.91 mmol) was brominated as described in Example 1 to give 3-bromo-7-difluoromethylimidazo[1,2-a]pyrimidine (0.95 g, 65%) as a white solid: $\delta_H$ (400 MHz, CDCl$_3$) 6.67 (1H, t, J 55), 7.34 (1H, d, J 7), 7.94 (1H, s), 8.57 (1H, d, J 7).

3-Bromo-7-difluoromethylimidazo[1,2-a]pyrimidine (248 mg, 1.00 mmol) was coupled with 3'-(4,4,5,5-tetramethyl-[1,3,2]dioxaborolan-2-yl)biphenyl-2-carbonitrile as described in Example 1 to give 3'-(7-difluoromethylimidazo[1,2-a]pyrimidin-3-yl)biphenyl-2-carbonitrile (201 mg, 58%) as a yellow powder: $\delta_H$ (400 MHz, CDCl$_3$) 6.67 (1H, t, J 55) 7.29 (1H, d, J 7), 7.52 (1H, td, J 9 and 1), 7.58–7.74 (5H, m), 7.87 (2H, m), 8.01 (1H, s), 9.12 (1H, d, J 7); m/z (ES$^+$) 347 (M$^+$+H).

EXAMPLE 21

7-Methyl-3-[3-(pyridin-3-yl)phenyl]imidazo[1,2-a]pyrimidine

To a degassed solution of trifluoromethanesulfonic acid 3-(7-methyl-imidazo[1,2-a]pyrimidin-3-yl)phenyl ester (0.1 g, 0.28 mmol) in 1,4-dioxane (3 ml) was added potassium phosphate (0.119 g, 0.56 mmol), pyridine-3-boronic acid 1,3-propanediol cyclic ester (0.092 g, 0.56 mmol) and tetrakis(triphenylphosphine)palladium(0) (0.016 g, 13.8 mmol) and the mixture heated at 80° C. for 22 h. After cooling to ambient temperature the solvent was evaporated in vacuo. The residue was stirred with 10% methanol in dichloromethane and the solid material filtered off. The filtrate was applied to two preparative TLC plates (silica gel) and eluted with 6% methanol in dichloromethane. The appropriate band was collected and processed to give an oil which crystallised from diethyl ether as a white solid (26 mg): $\delta_H$ (400 MHz, CDCl$_3$) 2.67 (3H, s), 6.80 (1H, d, J 7), 7.42 (1H, td, J 8 and 1), 7.57 (1H, m), 7.65 (2H, m), 7.71 (1H, s), 7.86 (1H, s), 7.92 (1H, m), 8.53 (1H, d, J 7), 7.65 (1H, m), 8.89 (1H, s); m/z (ES$^+$) 287 (M$^+$+H).

EXAMPLE 22

7-Methyl-3-[3'-(5-methyl-[1,2,4]oxadiazol-3-yl)biphenyl-3-yl]imidazo[1,2-a]pyrimidine To a degassed solution of trifluoromethanesulfonic acid 3-(7-methyl-imidazo[1,2-a]pyrimidin-3-yl)phenyl ester (2.53 g, 7 mmol) in 1,4-dioxane (25 ml) was added potassium acetate (2.08 g, 21 mmol), bis(pinacolato)diboron (1.97 g, 7.8 mmol) and dichloro[1,1'-bis(diphenylphosphino)ferrocene]palladium(II) (0.258 g, 0.35 mmol) and the mixture heated at 80° C. for 22 h. After cooling to ambient temperature the reaction was poured into water, extracted with ethyl acetate (3×100 ml) and the combined organics were dried over magnesium sulfate. Filtration and evaporation in vacuo gave a dark oil which was chromatographed on silica gel, eluting with a gradient of 1 to 10% methanol in dichloromethane. Appropriate fractions were pooled and evaporated to give 7-methyl-3-[3-(4,4,5,5-tetramethyl-[1,3,2]dioxaborolan-2-yl)phenyl]imidazo[1,2-a]pyrimidine as a cream coloured solid (1.97 g): $\delta_H$ (400 MHz, CDCl3) 1.36 (12H, s), 6.77 (1H, d, J 7), 7.52 (1H, m), 7.59 (1H, m), 7.80 (1H, s), 7.87 (1H, m), 7.95 (1H, s), 8.50 (1H, d, J 7); m/z (ES$^+$) 336 (M$^+$+H).

To a degassed solution of 7-methyl-3-[3-(4,4,5,5-tetramethyl-[1,3,2]dioxaborolan-2-yl)phenyl]imidazo[1,2-a]pyrimidine (0.1 g, 0.29 mmol) in 1,4-dioxane (3 ml) was added 3-(3-bromophenyl)-5-methyl-[1,2,4]oxadiazole (0.142 g, 0.59 mmol) (prepared as described in WO 95/27692), potassium phosphate (189 mg, 0.89 mmol) and tetrakis(triphenylphosphine)palladium(0) (17 mg, 15 μmol) and the mixture heated at 90° C. for 18 h. After cooling to ambient temperature the solvent was evaporated in vacuo and the residue stirred with 10% methanol in dichloromethane. The solid material was removed by filtration and the filtrate applied to two preparative TLC plates (silica gel) and eluted with 5% methanol in dichloromethane. The appropriate band was collected and processed, affording a solid which was recrystallised from dichloromethane/ethyl acetate/isohexane to give 7-methyl-3-[3'-(5-methyl-[1,2,4]oxadiazol-3-yl)biphenyl-3-yl]imidazo[1,2-a]pyrimidine as a cream coloured solid (32 mg): $\delta_H$ (400 MHz, CDCl$_3$) 2.67 (3H, s), 2.68 (3H, s), 6.79 (1H, d, J 7), 7.60–7.80 (5H, m), 7.87 (1H, s), 7.92 (1H, m), 8.10 (1H, dd, J 7 and 1), 8.32 (1H, s), 8.52 (1H, d, J 7); m/z (ES$^+$) 368 (M$^+$+H).

EXAMPLE 23

7-Methyl-3-[2'-(3-methyl-[1,2,4]oxadiazol-5-yl)biphenyl-3-yl]imidazo[1,2-a]pyrimidine To activated molecular sieves (2.0 g, 4 Å powdered) was added ethanol (20 ml) followed by sodium metal (0.435 g, 18.9 mmol), and the mixture heated at reflux for 15 min. After cooling to ambient temperature, acetamide oxime (1.4 g, 18.9 mmol) was added and the suspension stirred for 15 min. Methyl 2-bromobenzoate (1.32 ml, 9.5 mmol) was added and the mixture heated at reflux for 2 h. The reaction was poured into water and extracted with ethyl acetate. The organic phase was separated, dried over magnesium sulfate, filtered and evaporated to give a white solid. The crude product was purified by crystallisation from ethyl acetate/isohexane to give 5-(2-bromophenyl)-3-methyl-[1,2,4]oxadiazole as a white solid (0.76 g): $\delta_H$ (400 MHz, CDCl$_3$) 2.52 (3H, s), 7.45 (2H, m), 7.76 (1H, dd, J 7.8 and 1.2), 7.97 (1H, dd, J 7.8 and 1.2); m/z (ES$^+$) 239:241 (1:1) (M$^+$+H).

7-Methyl-3-[3-(4,4,5,5-tetramethyl-[1,3,2]dioxaborolan-2-yl)phenyl]-imidazo[1,2-a]pyrimidine (0.1 g, 0.29 mmol) was coupled to 5-(2-bromophenyl)-3-methyl-[1,2,4]oxadiazole (0.142 g, 0.59 mmol) as described in Example 22 and purified by mass-directed preparative HPLC to give 7-methyl-3-[2'-(3-methyl-[1,2,4]oxadiazol-5-yl)biphenyl-3-yl]imidazo[1,2-a]pyrimidine as its trifluoroacetate salt (21 mg): $\delta_H$ (400 MHz, CDCl$_3$) 2.40 (3H, s), 2.76 (3H, s), 7.07 (1H, d, J 7), 7.43–7.69 (7H, m), 8.03 (1H, s), 8.10 (1H, dd, J 7.8 and 1.1), 8.61 (1H, d, J 7); m/z (ES$^+$) 368 (M$^+$+H).

EXAMPLE 24

7-Methyl-3-[3-(thiazol-4-yl)phenyl]imidazo[1,2-a]pyrimidine

7-Methyl-3-[3-(4,4,5,5-tetramethyl-[1,3,2]dioxaborolan-2-yl)-phenyl]-imidazo[1,2-a]pyrimidine (0.1 g, 0.29 mmol) was coupled to 4-bromothiazole (98 mg, 0.59 mmol) as described in Example 22 except using N,N-dimethylacetamide in place of 1,4-dioxane as solvent. After cooling to ambient temperature the reaction was poured onto a strong cation exchange cartridge and eluted with methanol. The product was then eluted with a 2.0M solution of ammonia in methanol and evaporated in vacuo. The product was purified by mass-directed preparative HPLC to give 7-methyl-3-[3-(thiazol-4-yl)phenyl]imidazo[1,2-a]pyrimidine as its trifluoroacetate salt (24 mg): $\delta_H$ (400 MHz, CDCl$_3$) 2.77 (3H, s), 7.12 (1H, d, J 7), 7.51 (1H, m), 7.64–7.69 (2H, m), 8.05–8.09 (2H, m), 8.17 (1H, m), 8.65 (1H, d, J 7), 8.92 (1H, s); m/z (ES$^+$) 293 (M$^+$+H).

EXAMPLE 25

3'-(7-Methylimidazo[1,2-a]pyrimidin-3-yl)biphenyl-2-carbaldehyde Oxime

7-Methyl-3-[3-(4,4,5,5-tetramethyl-[1,3,2]dioxaborolan-2-yl)phenyl]-imidazo[1,2-a]pyrimidine (0.1 g, 0.29 mmol) was coupled to 2-bromobenzaldehyde oxime (98 mg, 0.59 mmol) as described in Example 24 to give 3'-(7-methylimidazo[1,2-a]pyrimidin-3-yl)biphenyl-2-carbaldehyde oxime as its trifluoroacetate salt (24 mg): $\delta_H$ (400 MHz, d$^6$DMSO) 2.71 (3H, s), 7.42–7.53 (4H, d, J 7), 7.68–7.79 (3H, m), 7.89 (1H, m), 8.01 (1H, s), 8.37 (1H, s), 8.65 (1H, d, J 7), 9.17 (1H, d, J 7.1), 11.36 (1H, bs); m/z (ES$^+$) 329 (M$^+$+H).

EXAMPLE 26

3-[3-(7-Methylimidazo[1,2-a]pyrimidin-3-yl)phenyl]pyridine-2-carbonitrile

7-Methyl-3-[3-(4,4,5,5-tetramethyl-[1,3,2]dioxaborolan-2-yl)phenyl]-imidazo[1,2-a]pyrimidine (0.1 g, 0.29 mmol) was coupled to 3-bromopyridine-2-carbonitrile (0.11 g, 0.59 mmol) as described in Example 24. The crude product was applied to two preparative plates (silica gel) and eluted with 5% methanol in dichloromethane. The appropriate band was collected and processed, affording a solid which was recrystallised from dichloromethane/ethyl acetate/isohexane to give 3-[3-(7-methylimidazo[1,2-a]pyrimidin-3-yl)phenyl]pyridine-2-carbonitrile as a white solid (31 mg): $\delta_H$ (400 MHz, CDCl$_3$) 2.67 (3H, s), 6.80 (1H, d, J 7), 7.55 (1H, td, J 8 and 1), 7.63–7.73 (3H, m), 7.77 (1H, m), 7.86 (1H, s), 7.94 (1H, dd, J 8 and 1.6), 8.75 (1H, d, J 1.6), 8.80 (1H, d, J 7); m/z (ES$^+$) 312 (M$^+$+H).

EXAMPLE 27

7-Methyl-3-[3-(pyridin-2-yl)phenyl]imidazo[1,2-a]pyrimidine

7-Methyl-3-[3-(4,4,5,5-tetramethyl-[1,3,2] dioxaborolan-2-yl)phenyl]-imidazo[1,2-a]pyrimidine (0.1 g, 0.29 mmol) was coupled to 2-bromopyridine (55 μl, 0.59 mmol) as described in Example 26 to give 7-methyl-3-[3-(pyridin-2-yl)phenyl]imidazo[1,2-a]pyrimidine as a white solid (30 mg): $\delta_H$ (400 MHz, CDCl$_3$) 2.67 (3H, s), 6.79 (1H, d, J 7), 7.30 (1H, m 7.55–7.65 (2H, m), 7.77–7.81 (2H, m), 7.87 (1H, s), 8.00 (1H, dd, J 8 and 1.6), 8.19 (1H, d, J 1.5), 8.57 (1H, d, J 7), 8.71 (1H, d, J 1.6); m/z (ES$^+$) 287 (M$^+$+H).

EXAMPLE 28

7-Methyl-3-[3-(thiazol-2-yl)phenyl]imidazo[1,2-a] pyrimidine

7-Methyl-3-[3-(4,4,5,5-tetramethyl-[1,3,2]dioxaborolan-2-yl)phenyl]-imidazo[1,2-a]pyrimidine (0.1 g, 0.29 mmol) was coupled to 2-bromothiazole (52 μl, 0.59 mmol) as described in Example 26 to give 7-methyl-3-[3-(pyridin-2-yl)phenyl]imidazo[1,2-a]pyrimidine as a white solid (23 mg): $\delta_H$ (400 MHz, CDCl$_3$) 2.68 (3H, s), 6.81 (1H, d, J 7), 7.39 (1H, d, J 3.2), 7.57–7.63 (2H, m), 7.87 (1H, s), 7.91 (1H, d, J 3.2), 7.99 (1H, dd, J 8 and 1.6), 8.17 (1H, m), 8.57 (1H, d, J 7); m/z (ES$^+$) 293 (M$^+$+H).

EXAMPLE 29

7-Methyl-3-(2'-trifluoromethylbiphenyl-3-yl) imidazo[1,2-a]pyrimidine

Trifluoromethanesulfonic acid 3-(7-methylimidazo[1,2-a]pyrimidin-3-yl)phenyl ester (0.1 g, 0.28 mmol) was coupled to 2-trifluoromethylbenzeneboronic acid (52 μl, 0.59 mmol) as described in Example 21 to give 7-methyl-3-(2'-trifluoromethylbiphenyl-3-yl)-imidazo[1,2-a]pyrimidine as a white solid (35 mg): $\delta_H$ (400 MHz, CDCl$_3$) 2.65 (3H, s), 6.77 (1H, d, J 7), 7.39 (1H, m), 7.48–7.62 (6H, m), 7.78 (1H, d, J 7.2), 7.82 (1H, s), 8.52 (1H, d, J 7); m/z (ES$^+$) 354 (M$^+$+H).

EXAMPLE 30

3-(2'-Fluorobiphenyl-3-yl)-7-methylimidazo[1,2-a] pyrimidine

Trifluoromethanesulfonic acid 3-(7-methylimidazo[1,2-a]pyrimidin-3-yl)phenyl ester (0.1 g, 0.28 mmol) was coupled to 2-fluorobenzene-boronic acid (52 μl, 0.59 mmol) as described in Example 21 to give 3-(2'-fluorobiphenyl-3-yl)-7-methylimidazo[1,2-a]pyrimidine as a white solid (104 mg): $\delta_H$ (400 MHz, CDCl$_3$) 2.67 (3H, s), 6.78 (1H, d, J 7), 7.17–7.28 (2H, m), 7.37 (1H, m), 7.46–7.54 (2H, m), 7.60 (2H, m), 7.71 (1H, s), 7.85 (1H, s), 8.56 (1H,: d, J 7); m/z (ES$^+$) 304 (M$^+$+H).

EXAMPLE 31

4-Fluoro-3'-(7-methylimidazo[1,2-a]pyrimidin-3-yl) biphenyl-2-carbonitrile

7-Methyl-3-[3-(4,4,5,5-tetramethyl-[1,3,2]dioxaborolan-2-yl)phenyl]-imidazo[1,2-a]pyrimidine (0.2 g, 0.6 mmol) was coupled to 2-bromo-5-fluorobenzonitrile (179 mg, 0.9 mmol) as described in Example 26 to give 4-fluoro-3'-(7-methylimidazo[1,2-a]pyrimidin-3-yl)biphenyl-2-carbonitrile as a white solid (85 mg): $\delta_H$ (400 MHz, CDCl$_3$) 2.67 (3H, s), 6.83 (1H, d, J 7), 7.20 (1H, dt, J 8.9 and 3), 7.50–7.70 (6H, m), 7.84 (1H, s), 8.76 (1H, d, J 7); m/z (ES$^+$) 329 (M$^+$+H).

EXAMPLE 32

3-[3-(Imidazol-1-yl)phenyl]-7-trifluoromethylimidazo[1,2-a]pyrimidine

To a cooled (−78° C.) solution of 3-bromo-7-trifluoromethyl-imidazo[1,2-a]pyrimidine (1.0 g, 3.78 mmol) in tetrahydrofuran (20 ml) was added isopropylmagnesium chloride (2.08 ml of a 2.0M solution in tetrahydrofuran, 4.16 mmol). After stirring for 5 min tributyltin chloride (1.2 ml, 4.42 mmol) was added and the reaction stirred for 10 min at −78° C. then allowed to warm to ambient temperature to give a solution of 3-tributylstannyl-7-trifluoromethylimidazo[1,2-a] pyrimidine in tetrahydrofuran (ca. 0.15M): m/z (ES$^+$) 474, 476, 478 (M$^+$+H).

To a degassed solution of 3-tributylstannyl-7-trifluoromethyl-imidazo[1,2-a]pyrimidine (1.4 mmol) was added 1-(3-bromophenyl)-1H-imidazole (0.60 g, 2.7 mmol) (prepared by the method of A. Johnson et al., *J. Med. Chem.*, 1969, 12(5), 1024–8) and tetrakis(triphenylphosphine)-palladium(0) (218 mg, 0.18 mmol) and the mixture heated at reflux for 18 h. The crude reaction was adsorbed onto silica and chromatographed on silica, eluting on a gradient of 1 to 5% methanol in dichloromethane, to give a yellow oil. Crystallisation from ethyl acetatelisohexane afforded 3-[3-(imidazol-1-yl)phenyl]-7-trifluoromethylimidazo[1,2-a] pyrimidine (0.098 g) as a white solid: $\delta_H$ (400 MHz; DMSO) 7.15 (1H, s), 7.53 (1H, d, J 7.4), 7.73 (1H, dd, J 3.1 and 1.6), 7.74 (1H, d, J 0.8), 7.78–7.81 (1H, m), 7.89 (1H, t, J 1.4), 8.08 (1H, dd, J 1.6 and 1.2), 8.39 (2H, d, J 7.0), 9.44 (1H, d, J 6.7); m/z (ES$^+$) 330 (M$^+$+H).

EXAMPLE 33

3-[3-([1,2,4]Triazol-1-yl)phenyl]-7-trifluoromethylimidazo[1,2-a]pyrimidine

A suspension of 3-bromophenylhydrazine hydrochloride (3.78 g, 17 mmol) in formamide (15 ml) was heated at 140° C. for 16 h. The reaction mixture was cooled to ambient temperature, diluted into dichloromethane (100 ml) and washed with water (2×100 ml). The organic phase was dried over anhydrous magnesium sulfate, filtered and evaporated to dryness to give 1-(3-bromophenyl)-1H-[1,2,4]triazole (3.44 g) as a tan solid: $\delta_H$ (400 MHz, CDCl$_3$) 8.57 (1H, s), 8.11 (1H, s), 7.90 (1H, t, J 2), 7.62–7.64 (1H, m), 7.53–7.55 (1H, m), 7.38 (1H, t, J 8).

1-(3-Bromophenyl)-1H-[1,2,4]triazole (1.7 g, 7.6 mmol) was coupled to 3-tributylstannyl-7-trifluoromethylimidazo [1,2-a]pyrimidine (3.8 mmol) by the method of Example 32. Purification by chromatography on silica gel eluting with dichloromethane on a gradient of methanol (1–3%), then crystallisation from toluene/isohexane, gave 3-[3-([1,2,4] triazol-1-yl)-phenyl]-7-trifluoromethylimidazo[1,2-a] pyrimidine as an off-white solid: $\delta_H$ (400 MHz, DMSO) 9.43 (1H, d, J 7), 9.41 (1H, s), 8.38 (1H, s), 8.30 (1H, s), 8.26–8.28 (1H, m), 7.97–8.00 (1H, m), 7.76–7.81 (2H, m), 7.56 (1H, d, J 7); m/z (ES$^+$) 331 (M$^+$+H).

EXAMPLE 34

3-[2'-([1,2,4]Triazol-1-yl)biphenyl-3-yl]-7-trifluoromethylimidazo[1,2-a]pyrimidine A suspension of 2-bromophenylhydrazine hydrochloride (5.0 g, 22 mmol) in formamide (10 ml) was heated at 140° C. for 16 h. The reaction mixture was cooled to ambient temperature, diluted into dichloromethane (50 ml) and washed with water (3×20 ml). The organic phase was dried over anhydrous magnesium sulfate, filtered and evaporated to dryness. Purification by chromatography on silica gel eluting with dichloromethane gave 1-(2-bromophenyl)-1H-[1,2,4]triazole (4.80 g) as a tan solid: $\delta_H$ (400 MHz, CDCl$_3$) 8.49 (1H, s), 8.14 (1H, s), 7.76 (1H, dd, J 1 and 8), 7.44–7.53 (2H, m), 7.34–7.39 (1H, m).

To a degassed solution of 1-(2-bromophenyl)-1H-[1,2,4] triazole (1.0 g, 4.5 mmol) in toluene (50 ml) was added hexabutylditin (4.7 ml, 9.3 mmol), then tetrakis(triphenylphosphine)palladium(0) (160 mg, 139 μmol) and the reaction heated at reflux for 48 h. The solvent was evaporated at reduced pressure and the residue chromatographed on silica gel eluting with dichloromethane to give 1-(2-tributylstannylphenyl)-1H-[1,2,4]triazole as an oil: m/z (ES$^+$) 434, 435, 436 (M$^+$+H).

To a degassed solution of 1-(2-tributylstannylphenyl)-1H-[1,2,4]triazole (300 mg, 0.7 mmol) in N,N-dimethylformamide (5 ml) was added 1,3-dibromobenzene (0.17 ml, 1.4 mmol), tetrakis(triphenylphosphine)palladium (0) (40 mg, 35 μmol), lithium chloride (293 mg, 6.9 mmol), then copper(I) iodide (13 mg, 69 μmol), and the mixture was heated at 80° C. for 5 h. The reaction was cooled to ambient temperature then poured into water (20 ml) and extracted with dichloromethane (3×20 ml). The combined organic phases were dried over anhydrous magnesium sulfate, filtered and evaporated to dryness. Purification by chromatography on silica gel eluting with dichloromethane on a gradient of methanol (0–1%), then by preparative thin-layer chromatography on silica gel using 5% methanol in dichloromethane as eluent, gave 1-(3'-bromobiphenyl-2-yl)-1H-[1,2,4]triazole as a colourless gel: m/z (ES$^+$) 300, 302 (M$^+$+H).

1-(3'-Bromobiphenyl-2-yl)-1H-[1,2,4]triazole (91 mg, 0.30 mmol) was coupled to 3-tributylstannyl-7-trifluoromethylimidazo[1,2-a]pyrimidine (0.25 mmol) by the method of Example 32. The product was obtained by preparative thin-layer chromatography on silica gel with 3% methanol in dichloromethane as eluent followed by high performance liquid chromatography to give 3-[2'-([1,2,4]triazol-1-yl)biphenyl-3-yl]-7-trifluoromethylimidazo[1,2-a]pyrimidine as a yellow solid: δ$_H$ (400 MHz, CDCl$_3$) 8.57 (1H, d, J 7), 7.95–8.11 (3H, m), 7.48–7.66 (7H, m), 7.35 (1H, J 8), 7.27 (1H, m); m/z (ES$^+$) 407 (M$^+$+H).

EXAMPLE 35

3'-[7-(Morpholin-4-ylmethyl)imidazo[1,2-a]porimidin-3-yl]biphenyl-2-carbonitrile To a solution of 3'-(7-hydroxymethyimidazo[1,2-a]pyrimidin-3-yl)biphenyl-2-carbonitrile (0.1 g, 0.31 mmol) in anhydrous dichloromethane under nitrogen was added carbon tetrabromide (153 mg, 0.46 mmol) and triphenylphosphine (121 mg, 0.46 mmol). The resultant mixture was stirred for 6 h after which time morpholine (67 μl, 0.77 mmol) was added and the reaction stirred for a further 18 h. The solvent was evaporated in vacuo and the residue purified by silica gel chromatography eluting with dichloromethane on a gradient of methanol (0–10%). Further purification by high performance liquid chromatography gave 3'-[7-(morpholin-4-ylmethyl)imidazo[1,2-a]pyrimidin-3-yl]biphenyl-2-carbonitrile trifluoroacetate salt (18.0 mg): δ$_H$ (400 MHz, d$^6$DMSO) 3.52 (4H, bs), 4.02 (4H, m), 4.64 (2H, s), 7.50–7.84 (9H, m), 8.12 (1H, bs), 9.17 (1H, s); m/z (ES$^+$) 396 (M$^+$+H).

EXAMPLE 36

4-Fluoro-3'-(7-trifluoromethylimidazo[1,2-a]pyrimidin-3-yl)biphenyl-2-carbonitrile 2-Bromo-5-fluorobenzonitrile and 3-nitrophenylboronic acid were coupled following the procedure in Example 1 to afford 4-fluoro-3'-nitro-biphenyl-2-carbonitrile as a black solid: δ$_H$ (360 MHz, CDCl$_3$) 7.39–7.48 (2H, m), 7.52–7.64 (1H, m), 7.71 (1H, dd, J 8 and 8), 7.89 (1H, d, J 8), 8.33–8.37 (2H, m).

4-Fluoro-3'-nitrobiphenyl-2-carbonitrile was reduced by treatment with tin(II) chloride in ethanol and tetrahydrofuran to give 3'-amino-4-fluorobiphenyl-2-carbonitrile as a brown solid: δ$_H$ (360 MHz, CDCl$_3$) 6.76 (1H, ddd, J 8, 2 and 2), 6.80 (1H, dd, J 2 and 2), 6.87 (1H, ddd, J 8, 1 and 1), 7.27 (1H, dd, J 8 and 8), 7.35 (1H, ddd, J 8, 8 and 3), 7.41–7.51 (2H, m).

3'-Amino-4-fluorobiphenyl-2-carbonitrile was bromodeaminated by treatment with 48% hydrobromic acid in 1,4-dioxane, then with sodium nitrite in water at <56° C., then with copper(I) bromide in 48% hydrobromic acid, to give 3'-bromo-4-fluorobiphenyl-2-carbonitrile as a white solid: δ$_H$ (400 MHz, CDCl$_3$) 7.35–7.40 (2H, m), 7.46–7.50 (3H, m), 7.59 (1H, dd, J 2 and 1), 7.64 (1H, dd, J 2 and 2).

3'-Bromo-4-fluorobiphenyl-2-carbonitrile was converted to 4-fluoro-3'-(4,4,5,5-tetramethyl-[1,3,2]dioxaborolan-2-yl)biphenyl-2-carbonitrile following the procedure in Example 1 to furnish a brown oil that crystallised on standing: δ$_H$ (400 MHz, CDCl$_3$) 1.36 (12H, s), 7.32–7.37 (1H, m), 7.43–7.54 (3H, m), 7.63–7.68 (1H, m), 7.88–7.90 (2H, m).

3-Bromo-7-trifluoromethylimidazo[1,2-a]pyrimidine was coupled with 4-fluoro-3'-(4,4,5,5-tetramethyl-[1,3,2]dioxaborolan-2-yl)biphenyl-2-carbonitrile as described in Example 1 to give 4-fluoro-3'-(7-trifluoromethylimidazo[1,2-a]pyrimidin-3-yl)biphenyl-2-carbonitrile (220 mg, 57%) as a yellow powder: δ$_H$ (400 MHz, CDCl$_3$) 7.29 (1H, d, J 7), 7.45 (1H, ddd, J 8, 1 and 1), 7.53 (1H, dd, J 8 and 3), 7.55–7.61 (2H, m), 7.65–7.67 (1H, m), 7.70–7.75 (1H, m), 7.77 (1H, s), 8.14 (1H, s), 9.14 (1H, d, J 7); m/z (ES$^+$) 383 (M$^+$+H).

EXAMPLE 37

4-Fluoro-3'-[7-(2-hydroxyprop-2-yl)imidazo[1,2-a]pyrimidin-3-yl]biphenyl-2-carbonitrile 2-(3-Bromoimidazo[1,2-a]pyrimidin-7-yl)propan-2-ol was coupled with 4-fluoro-3'-(4,4,5,5-tetramethyl-[1,3,2]dioxaborolan-2-yl)biphenyl-2-carbonitrile as described in Example 1 to give 4-fluoro-3'-[7-(2-hydroxyprop-2-yl)imidazo[1,2-a]pyrimidin-3-yl]biphenyl-2-carbonitrile (260 mg, 70%) as a yellow powder: δ$_H$ (360 MHz, CDCl$_3$) 1.61 (6H, s), 4.51 (1H, s), 7.07 (1H, d, J 7), 7.45 (1H, ddd, J 8, 1 and 1), 7.51–7.60 (3H, m), 7.63–7.69 (2H, m), 7.73 (1H, s), 7.90 (1H, s), 8.94 (1H, d, J 7); m/z (ES$^+$) 383 (M$^+$+H).

EXAMPLE 38

3-[3-(Pyridin-3-yl)phenyl]-7-trifluoromethylimidazo[1,2-a]pyrimidine

A mixture of 1,3-dibromobenzene (8.7 g, 36.8 mmol) and pyridine-3-boronic acid-1,3-propanediol cyclic ester (4.0 g, 24.5 mmol) in EtOH (60 ml) and toluene (60 ml) together with 2N Na$_2$CO$_3$ solution (24.5 ml) was degassed with a stream of N$_2$ for 10 min. Tetrakis(triphenylphosphine)palladium(0) (0.25 g, 0.22 mmol) was added and the reaction heated at reflux for 14 h. The mixture was concentrated under reduced pressure to remove the organic solvents. The organics were extracted with EtOAc (2×125 ml) and then washed with brine (75 ml), dried (MgSO$_4$), and concentrated under reduced pressure. The resulting crude residue was purified by column chromatography on silica, using 80% diethyl ether in hexane as the eluent, to yield 3-(3-bromophenyl)pyridine (3.66 g, 64%): δ$_H$ (360 MHz, CDCl$_3$) 7.30–7.42 (2H, m), 7.47–7.60 (2H, m), 7.72 (1H, s), 7.84 (1H, dt, J 8 and 2), 8.62 (1H, dd, J 4.8 and 1.5), 8.83 (1H, s).

A mixture of 3-(3-bromophenyl)pyridine (1.65 g, 7.1 mmol), bis(neopentyl glycolato)diborane (1.75 g, 7.8 mmol), KOAc (2.1 g, 21.2 mmol) and Pd(dppf)Cl$_2$ (288 mg, 5 mol %) in 1,4-dioxane (60 ml) was degassed with a stream of N$_2$ for 10 min and then heated at 110° C. for 16 h. The reaction mixture was concentrated under reduced pressure and diethyl ether (150 ml) was added. This was extracted with 4N NaOH (3×50 ml). These combined basic extracts were neutralised with conc. HCl and then extracted with dichloromethane (3×100 ml). The combined organic filtrates were washed with brine (50 ml) and dried (MgSO$_4$) to yield 3-[3-(5,5-dimethyl-[1,3,2]dioxaborinan-2-yl)phenyl]pyridine (1.63 mg, 87%): $\delta_H$ (360 MHz, CDCl$_3$) δ 1.04 (6H, s), 3.80 (4H, s), 7.38 (1H, dd, J 7.8 and 4.9), 7.47 (1H, t, J 7.8), 7.60–7.68 (1H, m), 7.84 (1H, d, J 7.4), 7.96 (1H, dt, J 7.8 and 2.0), 8.03 (1H, s), 8.58 (1H, dd, J 4.9 and 1.5), 8.85 (1H, s); m/z (ES$^+$) 267 (M+H$^+$).

A mixture of 3-bromo-7-trifluoromethylimidazo[1,2-a]pyrimidine (300 mg, 1.12 mmol), the foregoing boronate ester (602 mg, 2.24 mmol), 2N Na$_2$CO$_3$ solution (2.24 ml) and THF (4.5 ml) were degassed with a stream of N$_2$ for 5 min and then tetrakis(triphenyiphosphine)palladium(0) (130 mg 10 mol %) was added and the reaction was heated at 70° C. for 90 min. EtOAc (70 ml) was added and the mixture separated, washed with brine (20 ml), dried (MgSO$_4$) and concentrated under reduced pressure while dry loading onto MgSO$_4$. The residue was purified by column chromatography on silica using 70% EtOAc in hexanes containing 1% Et$_3$N and 1% MeOH as the eluent. The resulting material was taken up in MeOH and poured onto a strong cation exchange cartridge and eluted with methanol. The product was then eluted with 2.0M NH$_3$ in MeOH and evaporated while dry loading onto silica. Subsequent purification by column chromatography on silica using 2.5% MeOH in dichoromethane containing 1% NH$_3$ (aq.) gave 3-[3-(pyridin-3-yl)phenyl]-7-trifluoromethyelmidazo[1,2-a]pyrimiidine (120 mg, 31%): $\delta_H$ (360 MHz, d$_6$-DMSO) 7.48–7.58 (2H, m), 7.73 (1H, t, J 7.7), 7.81 (1H, d, J 7.7), 7.87 (1H, d, J 7.7), 8.12 (1H, s), 8.21 (1H, dt, J 8.1 and 2.0), 8.37 (1H, s), 8.62 (1H, dd, J 4.8 and d1.5), 9.03 (1H, d, J 2), 9.42 (1H, d, J 7.2); m/z (ES$^+$) 341 (M$^+$).

EXAMPLE 39

3-[3-([1,2,4]Triazol-4-yl)phenyl]-7-trifluoromethylimidazo[1,2-a]pyrimidine

A mixture of 1,2-bis[(diethylamino)methylene]hydrazine dihydrochloride (6.25 g, 29.0 mmol) and 3-bromoanile (5.0 g, 29.0 mmol) in toluene (100 ml) was heated at reflux for 14 h. The resulting mixture was cooled to room temperature and H$_2$O (100 ml) added. The layers were separated and the organics were washed with brine (75 ml), dried (MgSO$_4$), and concentrated under reduced pressure. The crude residue was purified by column chromatography on silica, using 2% MeOH in EtOAc as the eluent, to yield 4-(3-bromophenyl)-4H-[1,2,4]triazole (3.33 g, 51%): $\delta_H$ (360 MHz, CDCl$_3$) 7.32–7.38 (1H, m), 7.43 (1H, t, J 8), 7.59 (1H, s), 7.63 (2H, d, J 8), 8.47 (2H, s); m/z (ES$^+$) 223, 225 (1:1) (M$^+$).

4-(3-Bromophenyl)-4H-[1,2,4]triazole (2.5 g, 11.1 mmol), bis(neopentyl glycolato)diborane (2.77 g, 12.2 mmol), KOAc (3.3 g, 33.5 mmol) and Pd(dppf)Cl$_2$ (456 mg, 5 mol %) in 1,4-dioxane (100 ml) were reacted as described in Example 38 to yield 4-[3-(5,5-dimethyl-[1,3,2]dioxaborinan-2-yl)phenyl]-4H-[1,2,4]triazole (0.78 g, 27%): $\delta_H$ (360 MHz, CDCl$_3$) 1.04 (6H, s), 3.80 (4H, s), 7.40–7.50 (1H, m), 7.53 (1H, J 7.5), 7.80 (1H, s), 7.89 (1H, d, J 7.5), 8.57 (2H, s); m/z (ES$^+$) 257 (M$^+$+H).

A mixture of 3-bromo-7-trifluoromethylimidazo[1,2-a]pyrimidine (139 mg, 0.53 mmol), the foregoing boronate ester (269 mg, 1.05 mmol) and K$_3$PO$_4$ (483 mg, 2.1 mmol) in DMA (3 ml) was degassed with a stream of N$_2$ for 5 min and then tetrakis(triphenylphosphine)palladium(0) (60 mg, 10 mol %) was added and the reaction heated at 65° C. for 70 min. EtOAc (100 ml) was added and the mixture washed with H$_2$O (3×100 ml) and brine (100 ml), dried (MgSO$_4$) and concentrated under reduced pressure while dry loading onto silica. The residue was purified by column chromatography on silica using 5% MeOH in dichloromethane to yield 3-[3-([1,2,4]triazol-4-yl)phenyl]-7-trifluoromethylimidazo[1,2-a]pyrimidine (70 mg, 40%), which was then recrystallised from EtOAc/isohexanes: $\delta_H$ (400 MHz, d$_6$-DMSO) 7.55 (1H, d, J 7.2), 7.70–7.90 (3H, m), 8.16 (1H, s), 8.39 (1H, s), 9.24 (2H, s), 9.48 (1H, d, J 7.2); m/z (ES$^+$) 331 (M+H$^+$).

What is claimed is:

1. A compound of formula I, or a salt or prodrug thereof:

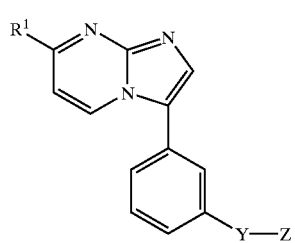

(I)

wherein

Y represents a chemical bond, an oxygen atom, or a —NH— linkage;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

2. A compound as claimed in claim 1 represented by formula IIA, and salts and prodrugs thereof:

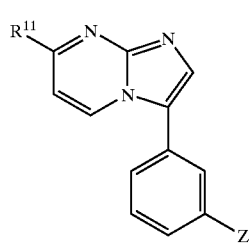

(IIA)

wherein

Z is as defined in claim 1;

R$^{11}$ represents hydrogen, C$_{1-6}$ alkyl, halo(C$_{1-6}$)alkyl, dihalo(C$_{1-6}$)alkyl, hydroxy(C$_{1-6}$)alkyl, C$_{1-6}$ akoxy(C$_{1-6}$)alkyl, di(C$_{1-6}$)alkoxy(C$_{1-6}$)alkyl, C$_{3-7}$ cycloalkyl, C$_{3-7}$ heterocycloalkyl(C$_{1-6}$)alkyl, heteroaryl, C$_{1-6}$ alkylheteroaryl, heteroaryl(C$_{1-6}$)alkyl, halogen, cyano, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R[5] represents hydrogen, $C_{1-6}$alkyl, hydroxy($C_{1-6}$)alkyl or di($C_{1-6}$)alkylamino($C_{1-6}$)alkyl.

3. A compound as claimed in claim 2 represented by formula IIB, and salts and prodrugs thereof:

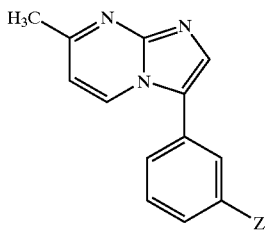

(IIB)

wherein Z is as defined in claim 1.

4. A compound as claimed in claim 2 represented by formula IIC, and salts and prodrugs thereof:

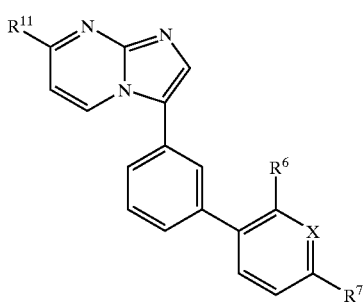

(IIC)

wherein

X represents CH or N;

R[6] represents fluoro, cyano, trifluoromethyl, methoxy, methyloxadiazolyl, triazolyl or —CR[2]=NOR[3];

R[7] represents hydrogen or fluoro;

R[2] represents hydrogen or methyl;

R[3] represents hydrogen, hydroxyethyl or dimethylamino-ethyl; and

R[11] is as defined in claim 2.

5. A compound as claimed in claim 2 represented by formula IID, and salts and prodrugs thereof:

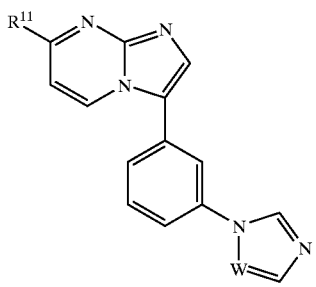

(IID)

wherein

W represents CH or N; and

R[11] is as defined in claim 2.

6. A compound selected from:
3'-(7-methylimidazo[1,2-a]pyrimidin-3-yl)biphenyl-2-carbonitrile;
and salts and prodrugs thereof.

7. A compound selected from:
3'-(imidazo[1,2-a]pyrimidin-3-yl)biphenyl-2-carbonitrile;
3'-(7-trifluoromethylimidazo[1,2-a]pyrimidin-3-yl)biphenyl-2-carbonitrile;
3'-[7-(1,1-dimethoxyethyl)imidazo[1,2-a]pyrimidin-3-yl]biphenyl-2-carbonitrile;
3'-(7-acetylimidazo[1,2-a]pyrimidin-3-yl)biphenyl-2-carbonitrile;
3'-(7-isopropylimidazo[1,2-a]pyrimidin-3-yl)biphenyl-2-carbonitrile;
3'-(7-cyclopropylimidazo[1,2-a]pyrimidin-3-yl)biphenyl-2-carbonitrile;
3'-(7-tert-butylimidazo[1,2-a]pyrimidin-3-yl)biphenyl-2-carbonitrile;
3'-(7-cyclobutylimidazo[1,2-a]pyrimidin-3-yl)biphenyl-2-carbonitrile;
3'-(7-methoxyimidazo[1,2-a]pyrimidin-3-yl)biphenyl-2-carbonitrile;
3'-(7-hydroxymethylimidazo[1,2-a]pyrimidin-3-yl)biphenyl-2-carbonitrile;
3'-(7-fluoromethylimidazo[1,2-a]pyrimidin-3-yl)biphenyl-2-carbonitrile;
3'-(7-formylimidazo[1,2-a]pyrimidin-3-yl)biphenyl-2-carbonitrile;
3'-(7-hydroxyiminomethylimidazo[1,2-a]pyrimidin-3-yl)biphenyl-2-carbonitrile;
3-(2'-cyanobiphenyl-3-yl)imidazo[1,2-a]pyrimidine-7-carbonitrile;
3-(2'-methoxybiphenyl-3-yl)-7-methylimidazo[1,2-a]pyrimidine;
3-(2'-cyanobiphenyl-3-yl)imidazo[1,2-a]pyrimidine-7-carboxylic acid methyl ester;
3'-(7-dimethoxymethylimidazo[1,2-a]pyrimidin-3-yl)biphenyl-2-carbonitrile;
3'-[7-([1,2,4]triazol-1-ylmethyl)imidazo[1,2-a]pyrimidin-3-yl]biphenyl-2-carbonitrile;
3'-(7-difluoromethylimidazo[1,2-a]pyrimidin-3-yl)biphenyl-2-carbonitrile;
7-methyl-3-[3-(pyridin-3-yl)phenyl]imidazo[1,2-a]pyrimidine;
7-methyl-3-[3'-(5-methyl-[1,2,4]oxadiazol-3-yl)biphenyl-3-yl]imidazo[1,2-a]pyrimidine;
7-methyl-3-[2'-(3-methyl-[1,2,4]oxadiazol-5-yl)biphenyl-3-yl]imidazo[1,2-a]pyrimidine;
7-methyl-3-[3-(thiazol-4-yl)phenyl]imidazo[1,2-a]pyrimidine;
3'-(7-methylimidazo[1,2-a]pyrimidin-3-yl)biphenyl-2-carbaldehyde oxime;
3-[3-(7-methylimidazo[1,2-a]pyrimidin-3-yl)phenyl]pyridine-2-carbonitrile;
7-methyl-3-[3-(pyridin-2-yl)phenyl]imidazo[1,2-a]pyrimidine;
7-methyl-3-[3-(thiazol-2-yl)phenyl]imidazo[1,2-a]pyrimidine;
7-methyl-3-(2'-trifluoromethylbiphenyl-3-yl)imidazo[1,2-a]pyrimidine;
3-(2'-fluorobiphenyl-3-yl)-7-methylimidazo[1,2-a]pyrimidine;
4-fluoro-3'-(7-methylimidazo[1,2-a]pyrimidin-3-yl)biphenyl-2-carbonitrile;

3-[3-(imidazol-1-yl)phenyl]-7-trifluoromethylimidazo[1,2-a]pyrimidine;

3-[3-([1,2,4]triazol-1-yl)phenyl]-7-trifluoromethylimidazo[1,2-a]pyrimidine;

3-[2'-([1,2,4]triazol-1-yl)biphenyl-3-yl]-7-trifluoromethylimidazo[1,2-a]pyrimidine;

3'-[7-(morpholin-4-ylmethyl)imidazo[1,2-a]pyrimidin-3-yl]biphenyl-2-carbonitrile;

and salts and prodrugs thereof.

8. A compound selected from:

4-fluoro-3'-(7-trifluoromethylimidazo[1,2-a]pyrimidin-3-yl)biphenyl-2-carbonitrile;

4-fluoro-3'-[7-(2-hydroxyprop-2-yl)imidazo[1,2-a]pyrimidin-3-yl]biphenyl-2-carbonitrile;

3-[3-(pyridin-3-yl)phenyl]-7-trifluoromethylimidazo[1,2-a]pyrimidine;

3-[3-([1,2,4]triazol-4-yl)phenyl]-7-trifluoromethylimidazo[1,2-a]pyrimidine;

and salts and prodrugs thereof.

9. A pharmaceutical composition comprising a compound of formula I as defined in claim 1 or a pharmaceutically acceptable salt thereof or a prodrug thereof in association with a pharmaceutically acceptable carrier.

10. A process for the preparation of a compound as claimed in claim 1, which comprises:

(A) reacting a compound of formula III with a compound of formula IV:

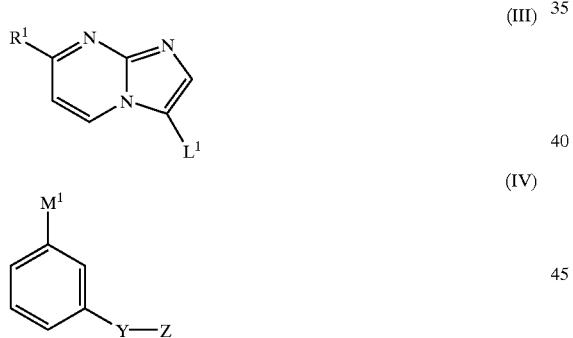

wherein Y, Z and $R^1$ are as defined in claim 1, $L^1$ represents a suitable leaving group, and $M^1$ represents a boronic acid moiety —$B(OH)_2$ or a cyclic ester thereof formed with an organic diol, or $M^1$ represents —$Sn(Alk)_3$ in which Alk represents a $C_{1-6}$ alkyl group; in the presence of a transition metal catalyst; or (B) reacting a compound of formula V with a compound of formula VI:

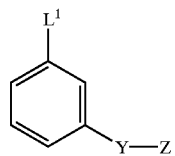

wherein Y, Z and $R^1$ are as defined in claim 1, and $L^1$ and $M^1$ are as defined above; in the presence of a transition metal catalyst; or (C) reacting a compound of formula VII with a compound of formula VIII:

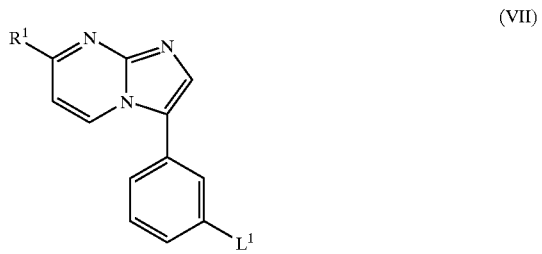

wherein Z and $R^1$ are as defined in claim 1, and $L^1$ and $M^1$ are as defined above; in the presence of a transition metal catalyst; or (D) reacting a compound of formula IX with a compound of formula X:

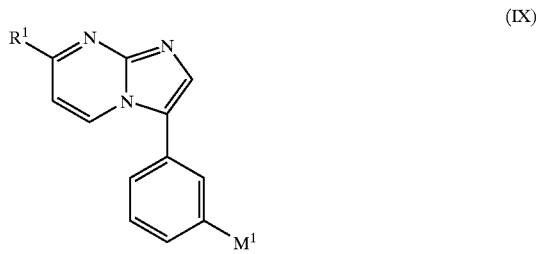

wherein Z and $R^1$ are as defined in claim 1, and $L^1$ and $M^1$ are as defined above; in the presence of a transition metal catalyst; or (E) reacting a compound of formula X as defined above with a compound of formula XI:

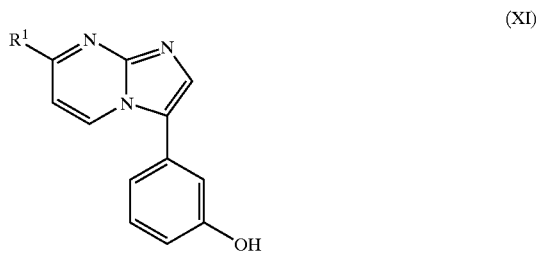

wherein $R^1$ is as defined in claim 1; or (F) reacting a compound of formula X as defined above with a compound of formula XII:

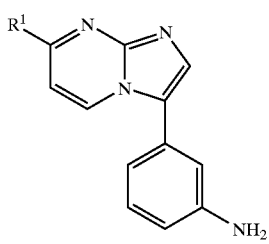
(XII)

wherein R¹ is as defined in claim 1; or (G) reacting a compound of formula XVI with a compound of formula XVII:

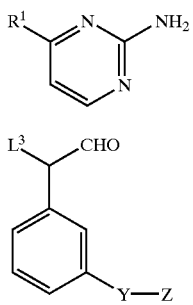
(XVI)
(XVII)

wherein Y, Z and R¹ are as defined in claim 1, and L³ represents a suitable leaving group; or (H) reacting a compound of formula XXI with a compound of formula XXII:

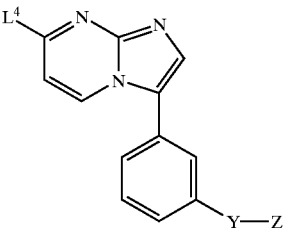
(XXII)

wherein Y and Z are as defined in claim 1, $R^{1a}$ represents an aryl or heteroaryl moiety, and L⁴ represents a suitable leaving group; in the presence of a transition metal catalyst; and (J) if desired, converting a compound of formula I initially obtained into a further compound of formula I by standard methods.

11. A method for the treatment of adverse neurological conditions which comprises administering to a patient in need of such treatment an effective amount of a compound of formula I as defined in claim 1 or a pharmaceutically acceptable salt thereof or a prodrug thereof.

* * * * *